(12) United States Patent
Bierman

(10) Patent No.: US 7,887,515 B2
(45) Date of Patent: *Feb. 15, 2011

(54) CATHETER ANCHORING SYSTEM

(75) Inventor: Steven F. Bierman, Del Mar, CA (US)

(73) Assignee: Venetec International, Inc., Covington, GA (US)

(*) Notice: Subject to any disclaimer, the term of this patent is extended or adjusted under 35 U.S.C. 154(b) by 561 days.
This patent is subject to a terminal disclaimer.

(21) Appl. No.: 10/996,870

(22) Filed: Nov. 23, 2004

(65) Prior Publication Data
US 2005/0075610 A1 Apr. 7, 2005
US 2007/0173768 A2 Jul. 26, 2007

Related U.S. Application Data

(63) Continuation of application No. 10/096,088, filed on Mar. 11, 2002, now Pat. No. 6,827,705, which is a continuation-in-part of application No. 09/809,460, filed on Mar. 15, 2001, now Pat. No. 6,786,892, which is a continuation of application No. 09/069,029, filed on Apr. 27, 1998, now Pat. No. 6,290,676, which is a continuation-in-part of application No. 08/753,277, filed on Nov. 25, 1996, now Pat. No. 5,827,230, which is a continuation of application No. 08/223,948, filed on Apr. 6, 1994, now Pat. No. 5,578,013, which is a continuation-in-part of application No. 08/121,942, filed on Sep. 15, 1993, now Pat. No. 5,456,671, which is a continuation-in-part of application No. 08/034,340, filed on Mar. 19, 1993, now Pat. No. 5,354,282, said application No. 10/096,088 is a continuation of application No. 09/165,367, filed on Oct. 2, 1998, now Pat. No. 6,837,875, which is a continuation-in-part of application No. 09/069,029, filed on Apr. 27, 1998, now Pat. No. 6,290,676.

(51) Int. Cl.
*A61M 5/32* (2006.01)

(52) U.S. Cl. ............... 604/180; 211/85.13; 206/564; 206/565

(58) Field of Classification Search ........... 604/174, 604/179, 180; 128/DIG. 6, DIG. 26; 211/85.13, 211/60.1, 63–64, 70.2, 85.18; 206/564–565
See application file for complete search history.

(56) References Cited

U.S. PATENT DOCUMENTS 2,402,306 A 6/1946 Turkel
(Continued)

FOREIGN PATENT DOCUMENTS

DE 2 341 297 4/1975
(Continued)

OTHER PUBLICATIONS

European Search Report for EP 06 11 4046 dated Feb. 12, 2007.
National Patent Services, Search Report re Patent Validity Study of U.S. Patent 5827230, pp. MDG 001319-MDG 001320, May 23, 2006.

(Continued)

*Primary Examiner*—Nicholas D Lucchesi
*Assistant Examiner*—Quynh-Nhu H Vu
(74) *Attorney, Agent, or Firm*—Knobbe, Martens, Olson & Bear LLP

(57) ABSTRACT

A catheter anchoring system is provided to securely anchor to a patient's skin a catheter and fluid supply tube interconnection. The anchoring system comprises a retainer configured to receive a catheter adaptor in a variety of positions. The adaptor interconnects the catheter and the fluid supply tube. In one embodiment the adaptor has a radial recess that circumscribes the adaptor. The anchoring system additionally includes a flexible, adhesive anchor pad which can supports a tube clip, as well as the retainer. The retainer includes a channel that is configured to receive the adaptor in a snap-fit manner. The retainer also includes a plurality of laterally arranged projections that extend from a channel wall and into a channel. Each radial recess is sized to receive and to capture at least a portion of the projection of the retainer so as to inhibit the adaptor from moving within the channel.

36 Claims, 14 Drawing Sheets

U.S. PATENT DOCUMENTS

| | | | |
|---|---|---|---|
| 2,525,398 A | 10/1950 | Collins | |
| 2,533,961 A | 12/1950 | Rousseau et al. | |
| 3,064,648 A | 11/1962 | Bujan | |
| 3,167,072 A | 1/1965 | Stone et al. | |
| 3,245,567 A | 4/1966 | Knight | |
| 3,394,954 A | 7/1968 | Sams | |
| 3,529,597 A | 9/1970 | Fuzak | |
| 3,589,361 A | 6/1971 | Loper et al. | |
| 3,677,250 A | 7/1972 | Thomas | |
| 3,686,896 A | 8/1972 | Rutter | |
| 3,766,915 A | 10/1973 | Rychlik | |
| 3,812,851 A | 5/1974 | Rodriguez | |
| 3,834,380 A | 9/1974 | Boyd | |
| 3,856,020 A | 12/1974 | Kovac | |
| 3,863,631 A | 2/1975 | Baldwin | |
| 3,900,026 A | 8/1975 | Wagner | |
| 3,901,226 A * | 8/1975 | Scardenzan | 128/888 |
| 3,906,946 A | 9/1975 | Nordstrom | |
| 3,920,001 A | 11/1975 | Edwards | |
| 3,942,228 A | 3/1976 | Buckman et al. | |
| 3,973,565 A | 8/1976 | Steer | |
| 4,004,586 A | 1/1977 | Christensen et al. | |
| D243,477 S | 2/1977 | Cutruzzula et al. | |
| 4,020,835 A | 5/1977 | Nordstrom et al. | |
| 4,037,599 A | 7/1977 | Raulerson | |
| 4,059,105 A | 11/1977 | Cutruzzula et al. | |
| 4,079,738 A | 3/1978 | Dunn et al. | |
| 4,082,094 A * | 4/1978 | Dailey | 604/93.01 |
| 4,114,618 A | 9/1978 | Vargas | |
| 4,116,196 A | 9/1978 | Kaplan et al. | |
| 4,123,091 A | 10/1978 | Cosentino et al. | |
| 4,129,128 A | 12/1978 | McFarlane | |
| 4,133,312 A | 1/1979 | Burd | |
| 4,142,527 A | 3/1979 | Garcia | |
| 4,161,177 A | 7/1979 | Fuchs | |
| 4,170,993 A | 10/1979 | Alvarez | |
| 4,182,455 A * | 1/1980 | Zurawin | 211/85.18 |
| 4,194,504 A | 3/1980 | Harms et al. | |
| D256,162 S | 7/1980 | Haerr et al. | |
| 4,224,937 A | 9/1980 | Gordon | |
| 4,230,109 A | 10/1980 | Geiss | |
| 4,250,880 A * | 2/1981 | Gordon | 604/180 |
| 4,275,721 A | 6/1981 | Olson | |
| 4,314,568 A | 2/1982 | Loving | |
| 4,316,461 A | 2/1982 | Marais et al. | |
| 4,324,236 A | 4/1982 | Gordon et al. | |
| 4,326,519 A | 4/1982 | D'Alo et al. | |
| 4,362,156 A | 12/1982 | Feller, Jr. et al. | |
| 4,392,853 A | 7/1983 | Muto | |
| 4,397,647 A * | 8/1983 | Gordon | 604/180 |
| 4,398,757 A | 8/1983 | Floyd et al. | |
| 4,405,163 A | 9/1983 | Voges et al. | |
| 4,405,312 A | 9/1983 | Gross et al. | |
| 4,435,174 A | 3/1984 | Redmond et al. | |
| 4,435,175 A | 3/1984 | Friden | |
| 4,439,193 A | 3/1984 | Larkin | |
| D273,993 S | 5/1984 | Schulte et al. | |
| 4,449,975 A | 5/1984 | Perry | |
| 4,453,933 A | 6/1984 | Speaker | |
| 4,470,410 A | 9/1984 | Elliott | |
| 4,474,559 A | 10/1984 | Steiger | |
| 4,480,639 A | 11/1984 | Peterson et al. | |
| 4,484,913 A | 11/1984 | Swauger | |
| 4,516,968 A | 5/1985 | Marshall et al. | |
| 4,561,857 A | 12/1985 | Sacks | |
| 4,563,177 A | 1/1986 | Kamen | |
| 4,585,435 A | 4/1986 | Vaillancourt | |
| 4,585,444 A | 4/1986 | Harris | |
| 4,631,056 A | 12/1986 | Dye | |
| 4,633,863 A | 1/1987 | Filips et al. | |
| 4,650,473 A | 3/1987 | Bartholomew et al. | |
| 4,660,555 A | 4/1987 | Payton | |
| 4,666,434 A | 5/1987 | Kaufman | |
| 4,693,710 A | 9/1987 | McCool | |
| 4,711,636 A | 12/1987 | Bierman | |
| 4,723,948 A | 2/1988 | Clark et al. | |
| 4,737,143 A | 4/1988 | Russell | |
| 4,742,824 A | 5/1988 | Payton et al. | |
| 4,743,231 A | 5/1988 | Kay et al. | |
| 4,752,292 A | 6/1988 | Lopez et al. | |
| 4,792,163 A | 12/1988 | Kulle | |
| 4,795,429 A | 1/1989 | Feldstein | |
| 4,826,486 A | 5/1989 | Palsrok et al. | |
| 4,834,702 A | 5/1989 | Rocco | |
| 4,834,716 A | 5/1989 | Ogle, II | |
| 4,838,858 A | 6/1989 | Wortham et al. | |
| D302,304 S | 7/1989 | Kulle et al. | |
| 4,846,807 A | 7/1989 | Safadago | |
| 4,852,844 A | 8/1989 | Villaveces | |
| 4,857,058 A | 8/1989 | Payton | |
| 4,863,432 A | 9/1989 | Kvalo | |
| 4,878,897 A | 11/1989 | Katzin | |
| 4,880,412 A | 11/1989 | Weiss | |
| 4,897,082 A | 1/1990 | Erskine | |
| 4,898,587 A | 2/1990 | Mera | |
| 4,919,654 A | 4/1990 | Kalt | |
| 4,934,375 A | 6/1990 | Cole et al. | |
| 4,941,882 A | 7/1990 | Ward et al. | |
| 4,955,864 A | 9/1990 | Hajduch | |
| 4,961,505 A * | 10/1990 | Moeller | 211/70.8 |
| 4,966,582 A | 10/1990 | Sit et al. | |
| 4,976,700 A | 12/1990 | Tollini | |
| 4,981,469 A | 1/1991 | Whitehouse et al. | |
| 4,997,421 A * | 3/1991 | Palsrok et al. | 604/174 |
| 5,024,665 A | 6/1991 | Kaufman | |
| 5,037,397 A | 8/1991 | Kalt et al. | |
| 5,037,398 A | 8/1991 | Buchanan | |
| 5,037,405 A | 8/1991 | Crosby | |
| D323,390 S | 1/1992 | Paine et al. | |
| 5,084,026 A | 1/1992 | Shapiro | |
| 5,098,048 A | 3/1992 | Chen | |
| 5,105,807 A | 4/1992 | Kahn et al. | |
| 5,112,313 A | 5/1992 | Sallee | |
| 5,135,506 A | 8/1992 | Gentelia et al. | |
| 5,137,519 A | 8/1992 | Littrell et al. | |
| 5,147,322 A | 9/1992 | Bowen et al. | |
| 5,147,322 A | 9/1992 | Bowen et al. | |
| 5,156,641 A | 10/1992 | White | |
| 5,192,273 A | 3/1993 | Bierman et al. | |
| 5,192,274 A | 3/1993 | Bierman | |
| 5,195,981 A | 3/1993 | Johnson | |
| 5,248,306 A | 9/1993 | Clark et al. | |
| 5,263,943 A | 11/1993 | Vanderbrook | |
| 5,267,967 A | 12/1993 | Schneider | |
| 5,279,578 A * | 1/1994 | Cooke | 604/192 |
| 5,292,013 A * | 3/1994 | Earl | 248/73 |
| 5,336,195 A | 8/1994 | Daneshvar | |
| 5,344,414 A | 9/1994 | Lopez et al. | |
| 5,354,282 A * | 10/1994 | Bierman | 604/180 |
| 5,380,293 A | 1/1995 | Grant | |
| 5,380,294 A | 1/1995 | Persson | |
| 5,380,301 A | 1/1995 | Prichard et al. | |
| 5,382,239 A | 1/1995 | Orr et al. | |
| 5,382,240 A | 1/1995 | Lam | |
| 5,395,344 A | 3/1995 | Beisang, III et al. | |
| 5,413,562 A | 5/1995 | Swauger | |
| 5,456,671 A | 10/1995 | Bierman | |
| 5,470,321 A | 11/1995 | Forster et al. | |
| 5,484,425 A | 1/1996 | Fischell et al. | |
| 5,496,283 A | 3/1996 | Alexander | |
| 5,507,535 A | 4/1996 | McKamey et al. | |
| 5,531,695 A | 7/1996 | Swisher | |
| 5,626,565 A | 5/1997 | Landis et al. | |
| 5,643,217 A | 7/1997 | Dobkin | |

| | | | |
|---|---|---|---|
| 5,681,290 A * | 10/1997 | Alexander | 604/180 |
| 5,685,859 A | 11/1997 | Kornerup | |
| 5,690,617 A | 11/1997 | Wright | |
| 5,885,251 A | 3/1999 | Luther | |
| D433,503 S | 11/2000 | Powers et al. | |
| 6,213,996 B1 | 4/2001 | Jepson et al. | |
| 6,216,885 B1 | 4/2001 | Guillaume | |
| 6,228,064 B1 | 5/2001 | Abita et al. | |
| 6,290,676 B1 * | 9/2001 | Bierman | 604/174 |
| 6,332,874 B1 | 12/2001 | Eliasen et al. | |
| 6,786,892 B2 * | 9/2004 | Bierman | 604/180 |
| 6,827,705 B2 * | 12/2004 | Bierman | 604/180 |
| 6,837,875 B1 * | 1/2005 | Bierman | 604/180 |
| 7,250,880 B2 | 7/2007 | Hurrell et al. | |

FOREIGN PATENT DOCUMENTS

| | | |
|---|---|---|
| EP | 0 169 704 A1 | 1/1986 |
| EP | 0 247 590 A2 | 12/1987 |
| EP | 0 263 789 A1 | 4/1988 |
| EP | 0 356 683 A1 | 3/1990 |
| EP | 0 367 549 A3 | 1/1991 |
| EP | 0 114 677 A3 | 11/1992 |
| EP | 0 720 836 | 7/1996 |
| FR | 2 598 625 A | 11/1987 |
| GB | 2 063 679 | 6/1981 |
| GB | 2 086 466 | 5/1982 |
| GB | 2 178 811 | 2/1987 |
| WO | WO 90/05559 | 5/1990 |
| WO | WO 91/16939 | 11/1991 |
| WO | WO 92/19309 | 11/1992 |
| WO | WO 92/19314 | 11/1992 |
| WO | WO 97/15337 | 5/1997 |
| WO | WO 97/15342 | 5/1997 |
| WO | WO 98/53872 | 12/1998 |

OTHER PUBLICATIONS

Complaint for Patent Infringement, *Venetec International, Inc. v. Medical Device Group, Inc.*, 8 pp., filed Jan. 13, 2006.

Answer, Affirmative Defenses and Counterclaims, *Venetec International, Inc. v. Medical Device Group, Inc., Medical Device Group, Inc. v. Venetec International, Inc.*, 9 pp., Mar. 8, 2006.

Defendant's Responses to Plaintiff's First Set of interrogatories (Nos. 1-9), *Venetec International, Inc. v. Medical Device Group, Inc., Medical Device Group, Inc. v. Venetec International, Inc.*, 19 pp., Jun. 12, 2006.

Cravens, et al., Urinary Catheter Management, American Family Physician, vol. 61, No. 2, pp. MDG 000273-MDG 000282, Jan. 15, 2000.

Dale® Foley Catheter Holder brochure, pp. MDG 000344-MDG 000346, 2002.

Grip-Lok™ Universal Tubing Securement brochure, pp. MDG 000348-MDG 000349, undated.

M.C. Johnson Co., Cath-Secure® brochure, pp. MDG 000357-MDG 000360, undated.

Grip-Lok Universal Tubing Securement brochure, pp. MDG 000364-MDG 000366, 2005-2006.

Expert Discusses Strategies to Prevent CAUTIs, Infection Control Today, pp. MDG 000603-MDG-000609, Jun. 2005.

Venetec International, Inc.'s Complaint for Patent Infringement, *Venetec International Inc. v. Medical Device Group, Inc.*, U.S. District Court for the Southern District of California, Case No. 06CV0083IEG, 9 pgs.

Medical Device Group, Inc.'s Answer, Affirmative Defenses and Counterclaims, *Venetec International Inc. v. Medical Device Group, Inc.*, U.S. District Court for the Southern District of California, Case No. 06CV0083IEG, 9 pgs.

Medical Device Group, Inc.'s Final Invalidity Contentions, *Venetec International Inc. v. Medical Device Group, Inc.*, U.S. Distric Court for the Southern District of California, Case No. 06CV0083IEG, 23 pgs.

Court's order on Claim Construction, *Venetec International Inc. v. Medical Device Group, Inc.*, U.S. District Court for the Southern District of California, Case No. 06CV0083IEG, 6 pgs.

Court's order granting Defendant's Motion for Summary Judgment of Non-infringement, *Venetec International Inc. v. Medical Device Group, Inc.*, U.S. District Court for the Southern District of California, Case No. 06CV0083IEG, 10 pgs.

Medical Device Group, Inc.'s Memorandum of Points and Authorities in Support of Defendant's Motion for Summary Judgment of Noninfringement, *Venetec International Inc. v. Medical Device Group, Inc.*, U.S. District Court for the Southern District of California, Case No. 06CV0083IEG, 25 pgs.

Venetec's Opposition to Medical Device Group, Inc.'s Motion for Summary Judgment of Noninfringement, *Venetec International Inc. v. Medical Device Group, Inc.*, U.S. District Court for the Southern District of California, Case No. 06CV0083IEG, 33 pgs.

* cited by examiner

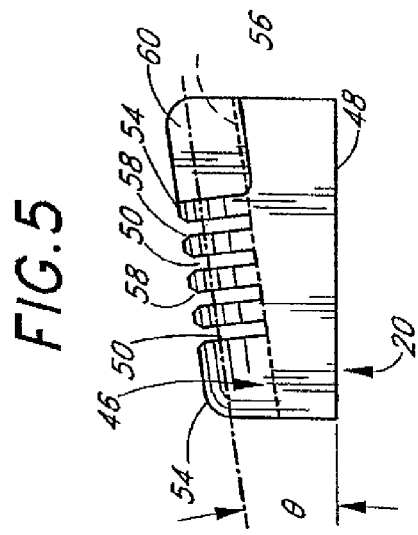
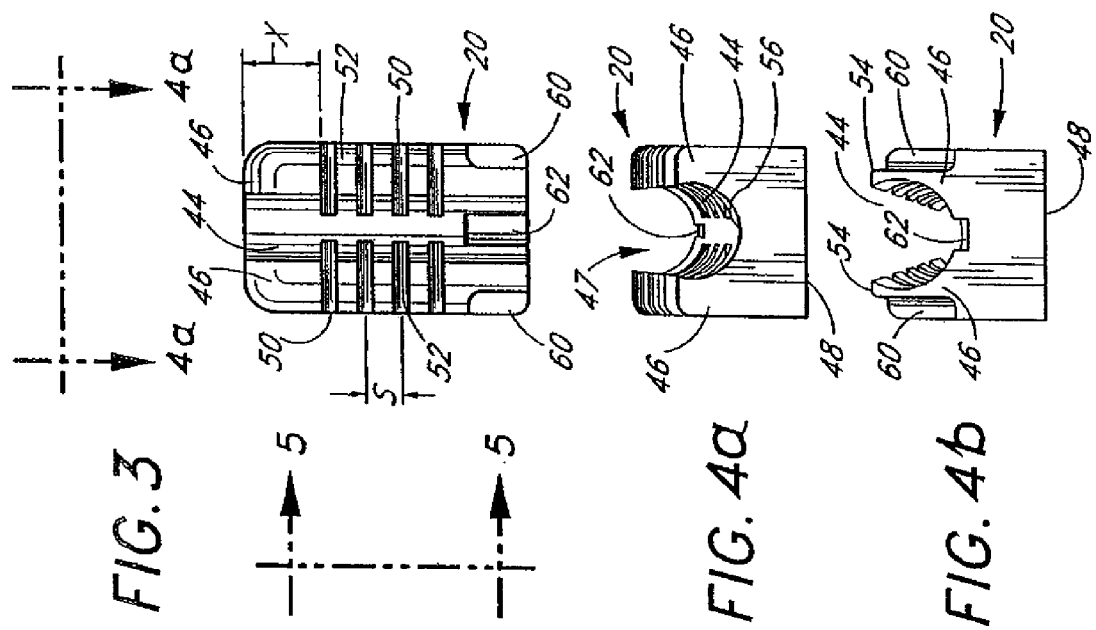

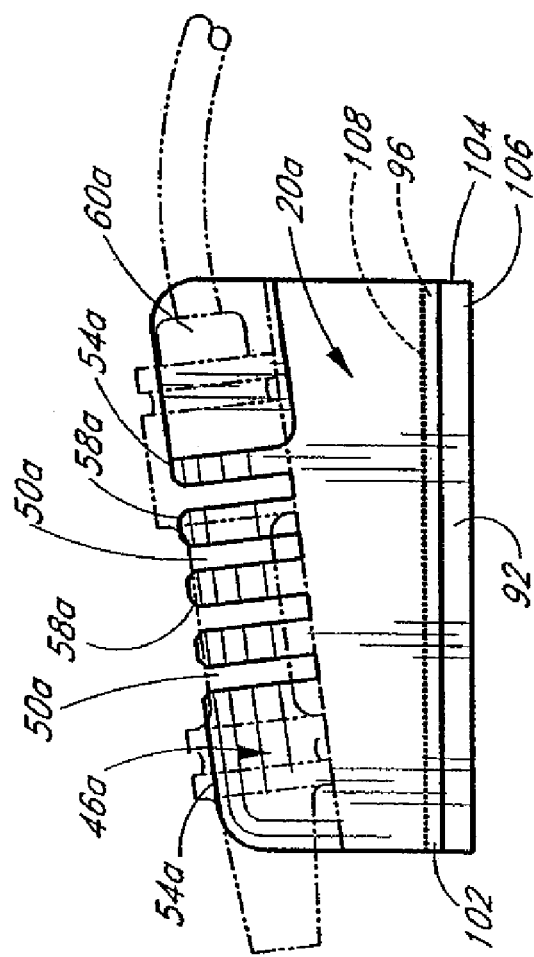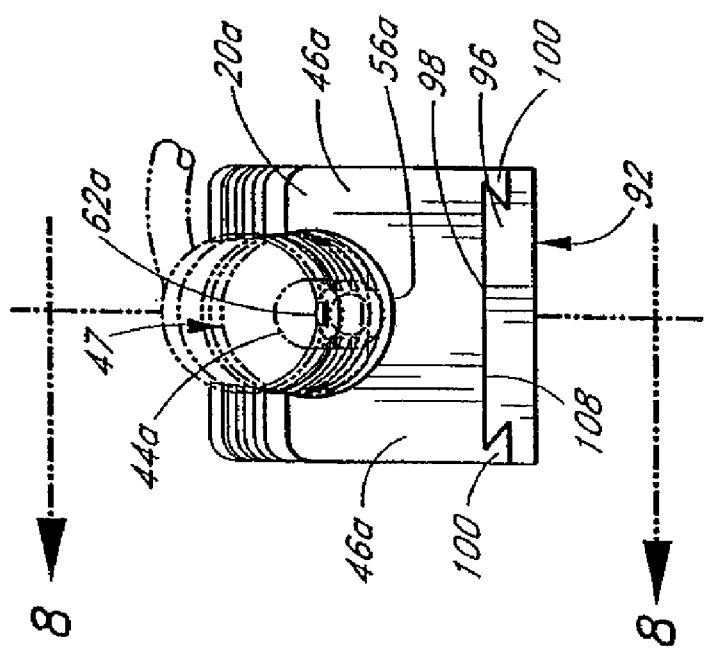
FIG. 7a
FIG. 7b

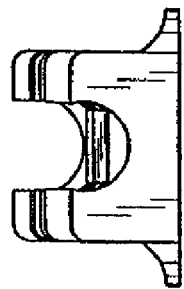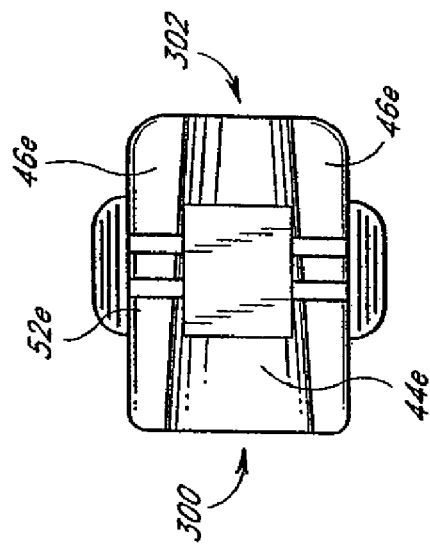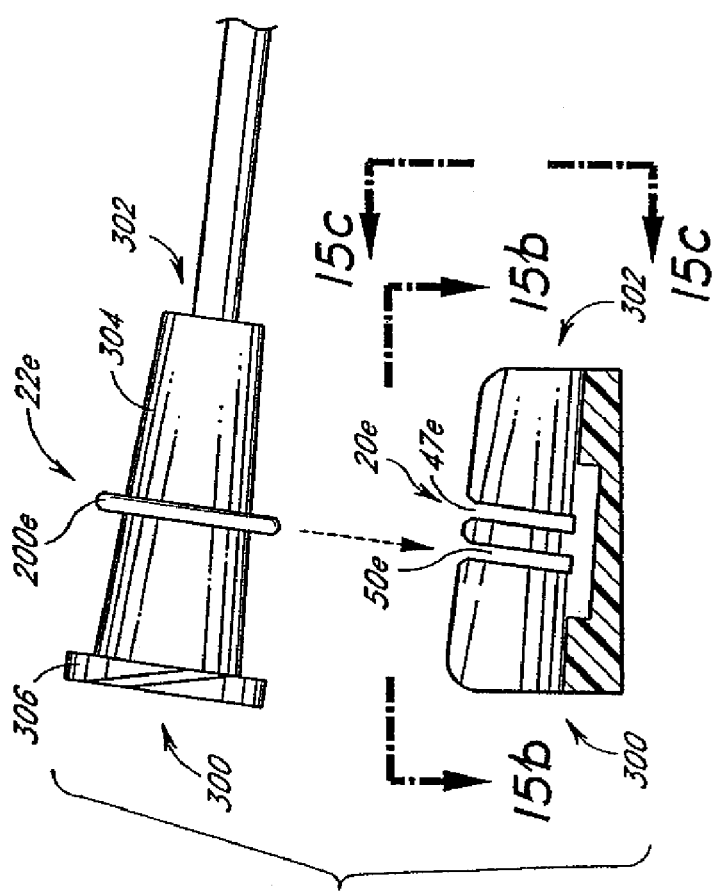

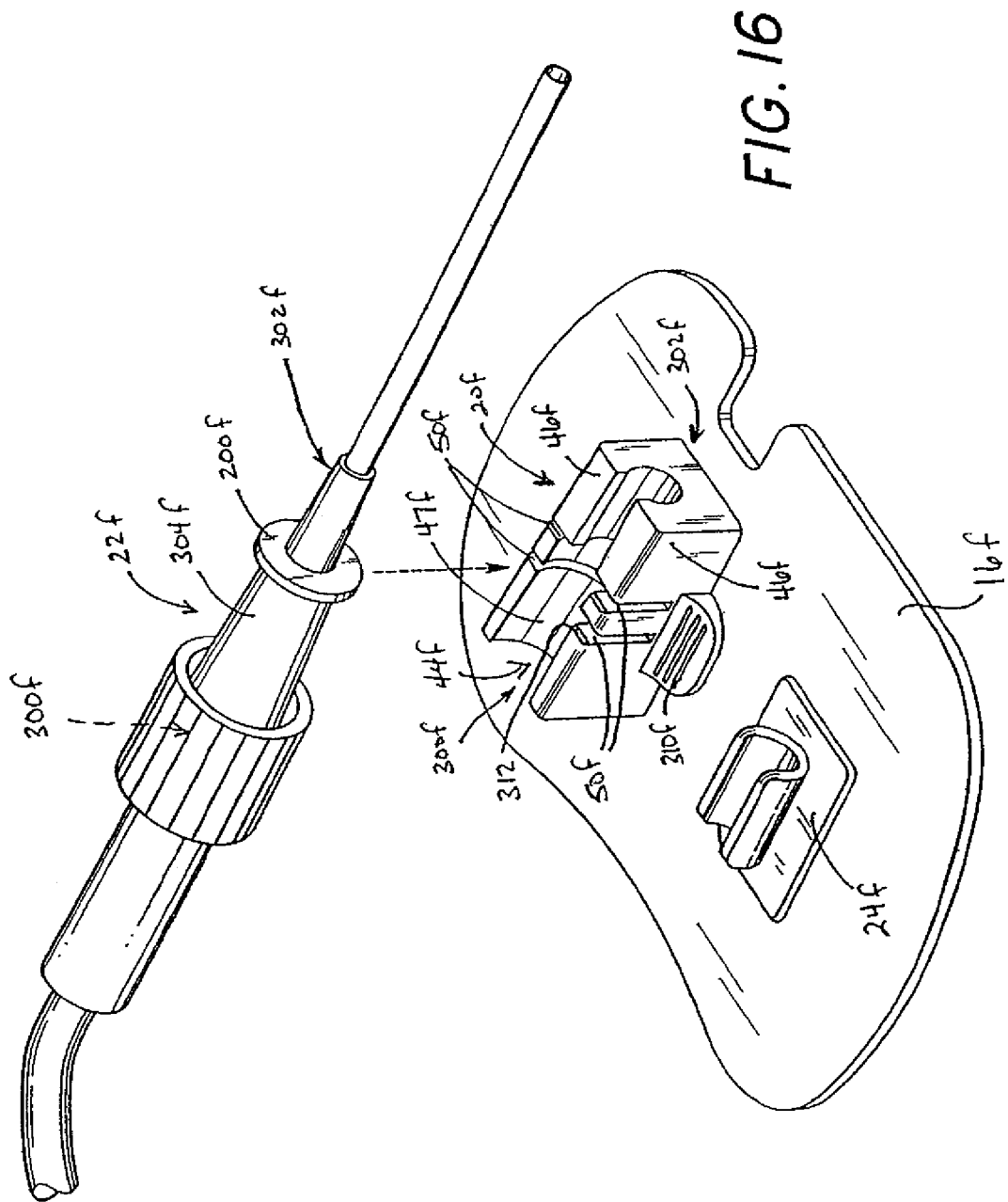

CATHETER ANCHORING SYSTEM

RELATED CASES

This is a continuation application of application Ser. No. 10/096,088 filed 11 Mar. 2002 now U.S. Pat. No. 6,827,705, which is a continuation-in-part of application Ser. No. 09/809,460 filed 15 Mar. 2001, now U.S. Pat. No. 6,786,892 issued on 7 Sep. 2004, which is a continuation of application Ser. No. 09/069,029 filed 27 Apr. 1998, now U.S. Pat. No. 6,290,676 issued on 18 Sep. 2001, which is a continuation-in-part of application Ser. No. 08/753,277 filed 25 Nov. 1996, now U.S. Pat. No. 5,827,230 issued on 27 Oct. 1998, which is a continuation of application Ser. No. 08/223,948 filed 6 Apr. 1994, now U.S. Pat. No. 5,578,013 issued 26 Nov. 1996, which is a continuation-in-part of application Ser. No. 08/121,942, filed 15 Sep. 1993, now U.S. Pat. No. 5,456,671 issued 10 Oct. 1995, which is a continuation-in-part of application Ser. No. 08/034,340 filed 19 Mar. 1993, now U.S. Pat. No. 5,354,282 issued 11 Oct. 1994, all of which are hereby incorporated by reference in their entireties. This application is a continuation application of copending application Ser. No. 10/096,088 filed 11 Mar. 2002, which is also a continuation of application Ser. No. 09/165,367 filed 2 Oct. 1998 now U.S. Pat. No. 6,837,875, which is a continuation-in-part of application Ser. No. 09/069,029 filed 27 Apr. 1998, now U.S. Pat. No. 6,290,676 issued on 18 Sep. 2001 and whose predecessor cases are listed above, all of which are hereby incorporated by reference in their entireties.

BACKGROUND OF THE INVENTION

1. Field of the Invention

The present invention relates in general to a percutaneous catheterization system, and, in particular, to a catheter anchoring system which securely interconnects an indwelling catheter with a tubing and securely anchors such interconnection to a patient's skin.

2. Description of Related Art

Medical treatment of patients commonly involves the use of percutaneously inserted catheters to direct fluids directly into the bloodstream, a specific organ or an internal location of the patient, or to monitor vital functions of the patient. For instance, intra-arteriosus catheters are commonly used to direct fluids and/or medication directly into the bloodstream of the patient. Epidural catheters are commonly used to direct anesthesia into an epidural space to anesthetize a specific location of the patient. Intervascular catheters are commonly used to monitor arterial blood pressure.

The fluid (e.g., parenteral liquid, medication or anesthesia) typically drains from a container positioned above the patient. The fluid flows through tubing and into an indwelling catheter. The catheter and fluid tubing are commonly removably attached by a conventional lure-type connector, such as the type described in U.S. Pat. No. 4,224,937.

In common practice, a health care provider, such as, for example, a nurse or doctor (for ease of description, as used herein the term "nurse" will refer to health care providers generally and will not be restrictive in meaning), uses adhesive or surgical tape to maintain the catheter in place on the skin of the patient. The connection between the tubing and the catheter is likewise maintained by use of tape.

The nurse may also form a safety loop in the tubing so that any tension applied to the tubing does not directly pass to the catheter cannula, but rather is absorbed by the slack of the safety loop. The nurse typically loosely tapes the loop to the skin of the patient.

This entire taping procedure takes several minutes of the valuable time of the health care provider. Furthermore, nurses commonly remove their gloves when taping because most nurse find such taping procedures difficult and cumbersome when wearing gloves.

The catheterization process often requires frequent disconnection between the catheter and the fluid supply tube. For instance, intravenous catheterization is frequently maintained for several days, depending upon the condition of the patient. The catheter tubing is generally replaced every 24 to 48 hours in order to maintain the sterility of the fluid and the free-flow of the fluid through the tubing. A nurse must thus frequently change the tubing and retape the connection. Moreover, the tape, which secures the catheter to the skin of the patient, often covers the cannula insertion point. The nurse must remove the tape to inspect the insertion point for inflammation or infection, and must then repeat the above-described taping procedure.

A great deal of valuable time is thus used in applying significant amounts of surgical tape to indwelling catheters. The frequent application and removal of surgical tape also commonly results in the excoriation of the skin of the patient in the area of the insertion.

A number of catheterization systems have recently been developed which improve the stabilization of the catheter system and obviate the need for frequent application and removal of surgical tape. One such system is disclosed by U.S. Pat. No. 5,192,273 issued to the present Applicant, which is hereby incorporated by reference.

The '273 patent discloses an adaptor which interconnects the catheter with a fluid supply tubing. The adaptor snaps into a base attached to the patient's skin by an adhesive pad. Specifically, a nurse presses the adaptor between upstanding legs of the base. Detents on the adaptor legs slide into corresponding annular grooves in the adaptor body to hold the adaptor to the base.

Although the base holds the adaptor securely in place, a nurse may have difficulty positioning and aligning the annular grooves of the adaptor with the detents on the base. Exigent circumstances may further exacerbate the difficulties associated with properly positioning the adaptor onto the base. Some nurses and other health care providers may also have trouble determining how to engage the catheter adaptor with the base.

SUMMARY OF THE INVENTION

The catheter anchoring system of the present invention provides an adaptor retainer which is not position or technique sensitive. That is, the nurse simply locates the catheter adaptor generally above the retainer, and presses the adaptor into the retainer. Engagement requires only coarse alignment of the adaptor with the retainer.

In accordance with one aspect of the present invention, an anchoring system is provided for use with a catheter having an adaptor with at least one recess. A retainer is provided to receive the adaptor. The retainer includes a channel that extends through the retainer about a longitudinal axis. The channel is configured to receive at least a portion of the adaptor in a snap-fit manner. At least one projection on the retainer extends into the channel in a direction generally normal to the longitudinal axis. The projection has a longitudinal length so dimensioned to substantially equal the longitudinal length of the recess of the adaptor. The cooperation between the projection of the retainer and the recess of the adaptor inhibit longitudinal movement of the adaptor relative to the retainer.

In accordance with another aspect of the present invention, an anchoring system is provided for use with a catheter having an adaptor with a recess. The retainer includes a channel that extends through the retainer about a longitudinal axis. The channel is configured to receive at least a portion of the adaptor in a snap-fit manner. At least one projection on the retainer extends into the channel in a direction generally normal to the longitudinal axis. The projection has a longitudinal length so dimensioned to substantially equal the longitudinal length of the recess of the adaptor. The cooperation between the projection of the retainer and the recess of the adaptor inhibit longitudinal movement of the adaptor relative to the retainer.

In accordance with yet another aspect of the present invention, an anchoring system is provided for use with a catheter having an adaptor with a radially extending member that projects from the fitting. The anchoring system comprises a retainer that includes first and second channel portions. The channel portions extend about a longitudinal axis, and each is configured to receive a corresponding portion of the catheter fitting. A plurality of lateral slots are positioned between the channel portions. Each lateral slot is dimensioned so as to receive the radially extending member of the catheter fitting to prevent the catheter from moving in a longitudinal direction. The lateral slots are also arranged next to each other along the longitudinal axis so as to provide multiple positions in the longitudinal direction in which to insert the radially extending member of the catheter fitting when positioning the catheter fitting within the retainer.

Another aspect of the present invention involves a catheterization system includes a catheter and a retainer to secure the catheter to a patient. The catheter includes a fitting with a radially extending member that projects from the fitting. The retainer includes first and second channel portions that extend about a longitudinal axis. Each channel portion generally has a truncated cross-sectional shape with an opening along the longitudinal axis. Each channel is also sized to surround at least a portion of the fitting through an arc of greater than 180° about the longitudinal axis. At least one lateral slot of the retainer extends generally perpendicular to the longitudinal axis and lies between the first and second channel portions. The slot has a longitudinal length so dimensioned to substantially equal the thickness of the radially extending member of catheter fitting and to be generally less than the combined longitudinal lengths of the first and second channel portions. This dimensional relationship between the channel portions and the slot provides lateral stability of the catheter fitting when the radially extending member is positioned within the lateral slot of the retainer.

In accordance with a further aspect of the present invention, a catheter anchoring system comprises a catheter adaptor, a retainer and a base pad which adheres to the skin of a patient and supports the retainer. The catheter adaptor comprises a tubular body connected to a radially extending support arm. The support arm in turn connects to a clip which pivots relative to the tubular body.

The retainer comprises a pair of opposing longitudinal walls. Each wall defines a series of slots. Each slot is sized such that a portion of the support arm of the catheter adaptor extends through the slot. The slot prevents the support arm from moving in a direction generally parallel to a longitudinal direction of the retainer.

The retainer further comprises a central channel which extends through the retainer about an axis which is generally parallel to the longitudinal axis. The channel is interposed between the opposing longitudinal walls and has a truncated circular cross-sectional shape. The central channel, in cross-section, is sized to encompass the tubular body through an angle greater than about 180N.

The anchoring system may additionally comprise a tube clip configured to receive a portion of the tube. The anchoring system may also comprise an S-clip having a plurality of retainers to secure a microbore tubing connected to the tube by the adaptor.

An additional aspect of the present invention provides a catheter anchoring system for securing an indwelling catheter within a body lumen of a patient and for securely interconnecting the indwelling catheter with a tube. The catheter anchoring system comprises a catheter adapter having a generally tubular body defined between distal and proximal ends. The distal end is configured to engage the catheter proximal end and the proximal end is configured to couple to a distal end of the supply tube. The catheter adapter additionally comprises a radially extending member which projects from an exterior surface of the tubular body in a radial direction.

A retainer of the catheter anchoring system comprises a longitudinal channel configured to receive the tubular body of the adapter in a snap fit manner. The retainer additionally comprises a plurality of lateral slots or projections which are sized to receive and to capture the radially extending member of the adapter with the adapter positioned within the channel. The slots can be formed in a variety of ways, such as by laterally arranging a plurality of gaps next to each other and through the opposing longitudinal walls of the retainer. The projections can similarly be formed in a variety of ways, such as by laterally arranging a plurality of projections next to each other from the opposing longitudinal walls of the retainer and projecting the projections into the channel. The retainer prevents the adapter from sliding in a longitudinal direction when one of the slots.

In a preferred embodiment, the radially extending member comprises a support arm which connects a clip to the tubular body. In an alternative preferred embodiment, the radially extending member comprises an annular collar which circumscribes the tubular body.

In accordance with a preferred method of anchoring an indwelling catheter/tube interconnection to a patient, an adapter is provided having a generally tubular body with a recess. An anchor pad is also provided with an adhesive back. The anchor pad supports a retainer configured to receive the adapter and has a series of lateral projections. The anchor pad is attached to the patient's skin proximate to an indwelling catheter. The recess of the adapter is positioned above the series of projections. The retainer is deflected so as to open the channel to a size sufficient to receive the adapter, and the adapter is inserted into the channel. The recess is inserted around at least a portion of one of the projections. The retainer is then permitted to spring back to an undeflected position such that the tubular body is captured within the retainer.

BRIEF DESCRIPTION OF THE DRAWINGS

These and other features of the invention will now be described with reference to the drawings of preferred embodiments which are intended to illustrate and not to limit the invention, and in which:

FIG. 3 is a top plan view of a retainer of the catheter anchoring system of FIG. 2;

FIG. 4a is a front elevational view of the retainer of FIG. 3;

FIG. 4b is a rear elevational view of the retainer of FIG. 3;

FIG. 5 is a side elevational view of the retainer of FIG. 3;

FIG. 7a is a front elevational view of a retainer and rail assembly of the catheter anchoring system of FIG. 6;

FIG. 7b is a side elevational view of the retainer and rail assembly of FIG. 6;

FIG. 8 is a cross-sectional view of the retainer and rail assembly taken along line 8-8 of FIG. 7a;

FIG. 15a is side elevational view of a catheterization system in accordance with another preferred embodiment of the present invention with a retainer of the catheterization system shown in cross-section;

FIG. 15b is a top plan view of the retainer of FIG. 15a as viewed in the direction of arrows 15b-15b;

FIG. 15c is a front end elevational view of the retainer of FIG. 15a as viewed in the direction of arrows 15c-15c; and FIG. 16 is a perspective view of a catheterization system configured in accordance with another embodiment of the present invention, and illustrates a catheter in a position separate from a retainer of the catheterization system;

DETAIL DESCRIPTION OF PREFERRED EMBODIMENTS

Figure 1:
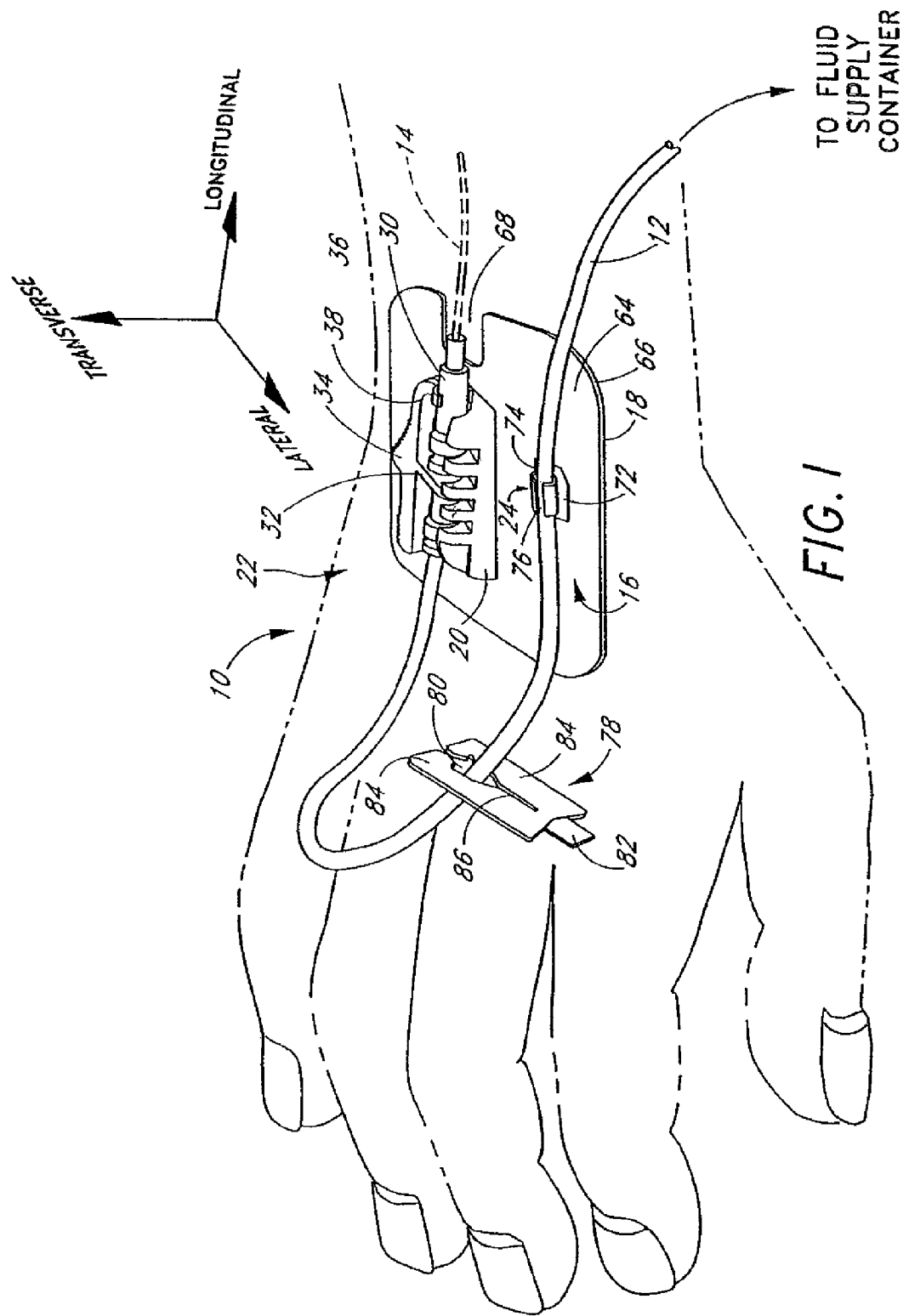
FIG. 1 is a perspective view of a catheter anchoring system in accordance with a preferred embodiment of the present invention, mounted on the back of a patient's hand.

FIG. 1 illustrates in perspective view a catheter anchoring system 10 in accordance with the present invention. The anchoring system 10 securely connects a tube 12 (e.g., a fluid supply tube) to an indwelling catheter 14 and maintains the catheter 14 in the desired indwelling position. The anchoring system 10 is designed for rapid attachment to the catheter 14 and to the patient, without requiring precise alignment or positioning of the components of the anchoring system 10.

Moreover, sturdy anchoring of the catheterization system is achieved without the use of surgical tape. For most catheterization, the anchoring system is attached to the patient only once. Although the fluid supply tubing 12 may be replaced every 24 to 48 hours for intravenous catheterization, the components of the anchoring system 10 attached to the patient remains in place. Thus, surgical tape need not be applied and removed from the patient's skin on multiple occasions.

The catheter anchoring system 10 principally comprises a flexible pad 16 having an adhesive bottom side 18 which attaches to the skin of a patient when used. The pad 16 supports a retainer 20. The retainer 20 is configured to receive and secure in place a catheter adaptor 22 which interconnects the hub 30 of an indwelling catheter 14 and the fluid supply tube 12 connected to a fluid supply container (not shown). The container maintains the fluid to be dispensed to the patient which is fed either by gravity or by pressure. A clamp (not shown) may be used to regulate the fluid flow through the tubing 12. The pad 16 may also support a tubing clip 24 which is used to retain a portion of tubing 12.

Although FIG. 1 illustrates the catheter anchoring system located on the back of a patient's hand (illustrated in phantom lines), it is contemplated that the present invention may be used for catheterization in other locations on the patient's body. For instance, the anchoring system may be used on the medial side of the wrist in connection with a radial artery. The anchoring system 10 may also be used for epidural catheterization, as discussed in detail below, and thus located on the anterior or posterior of the patient's torso.

FIG. 1 illustrates a longitudinal axis, a transverse axis and a lateral axis in relation to the catheter anchoring system 10 to facilitate the following description. Additionally, as used herein, "the longitudinal direction" refers to a direction substantially parallel to the longitudinal axis. "The lateral direction" and "the transverse direction" are in reference to the lateral axis and transverse axis, respectively. Also, "proximal" and "distal" are in reference to the proximity of the fluid supply container attached to the tube 12 (see FIG. 1). The individual components of the catheter anchoring system 10 will now be described in detail.

Catheter Adaptor

Figure 2:
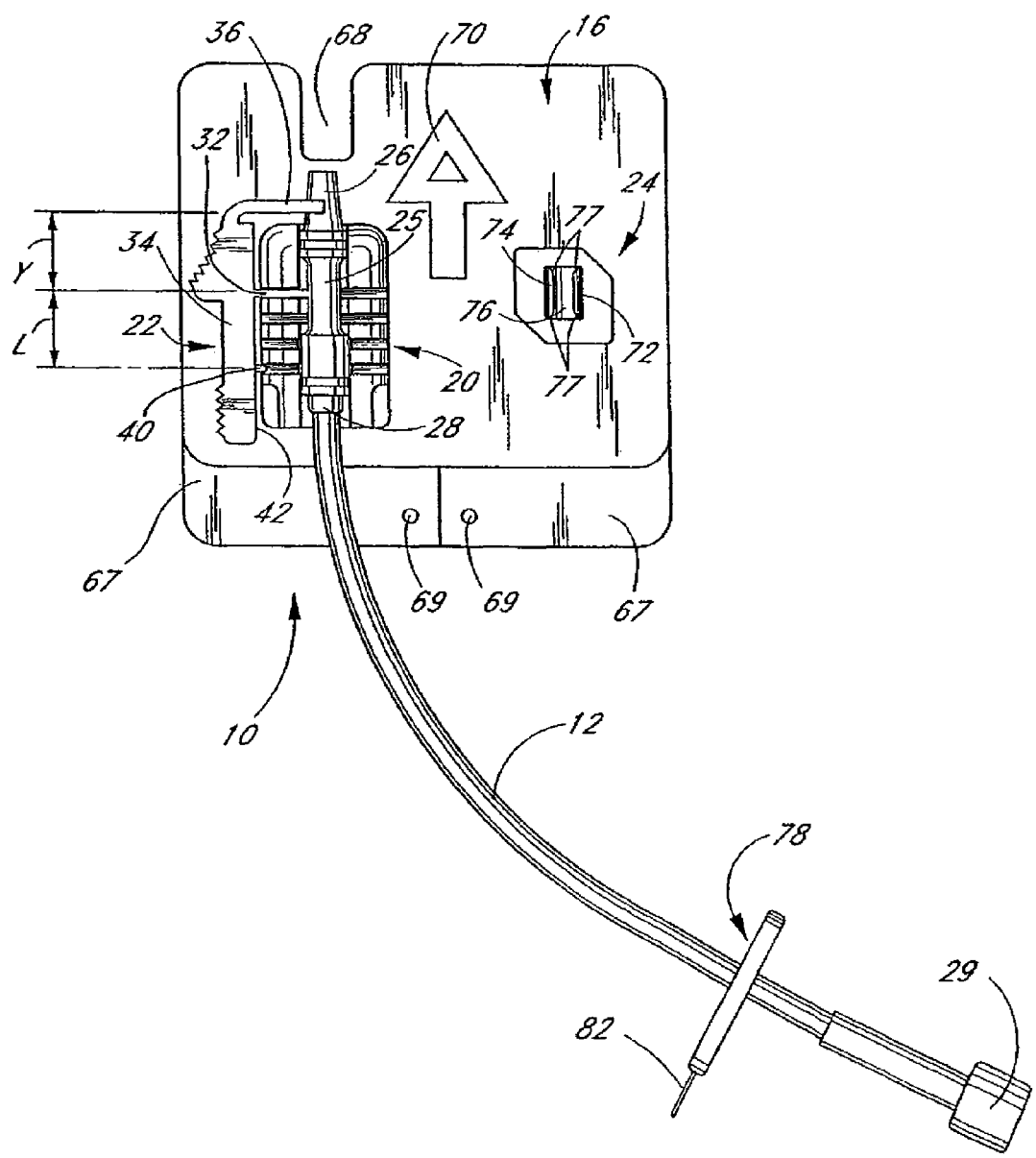
FIG. 2 is a top plan view of the catheter anchoring system of FIG. 1.

FIG. 1 illustrates the catheter adaptor 22 interconnected with a catheter 14. FIG. 2 illustrates the catheter adaptor 22 disconnected from catheter 14. Although these figures illustrate the adaptor 22 as the type disclosed in U.S. Pat. No. 5,193,273, it is contemplated that other types of adaptors can be used as well with the present catheter anchoring system 10. For instance, the catheter adaptor 22 could be a lure-type adaptor, such as the type illustrated by FIG. 11 and described below, or a lure-lock type catheter adaptor 22, such as the type illustrated by FIG. 14 and described below. It is contemplated that those skilled in the art could readily select the type of catheter adaptor 22 to be used with the present catheter anchoring system 10 depending on the particular application (e.g., venous, arterial, epidural, peripheral, etc.) of the anchoring system 10.

As best seen in FIG. 2, the adaptor 22 comprises a tubular body 25 defined between a distal end 26 and a proximal end 28. The proximal end 28 is adapted to receive a distal end of the tube 12. In an exemplary embodiment, at least a portion the fluid supply tube is permanently attached to the body proximal end 28. As shown in FIG. 2, the proximal end of the tubing may then include a standard lure-type connector 29 to connect into a fluid supply line 12.

The distal end 26 is configured to engage the proximal hub 30 of the catheter 14 (see FIG. 1) or any lure-type connector. Although FIG. 2 illustrates the distal end of the adaptor 22 as having a frusto-conical shape configured to engage a standard lure-type catheter hub 30, it is contemplated that the distal end 26 could be configured as well to engage other types of catheter connectors, such as, for example, a Toughy-Bourst adaptor.

A support arm 32 extends outwardly from the tubular body 25 in cantilever fashion. The support arm 32 supports, on a radially outer end of the arm 32, a clip support element (not shown) that extends generally parallel to and is spaced from a longitudinal axis of the tubular body 25.

FIG. 2 further illustrates a clip 34 of the catheter adaptor. The clip 34 attaches to and slides over the clip support element in the longitudinal direction. The clip 34 includes a distal latch 36 which has a generally forked shape to engage a outer surface of the catheter hub 30 distal of a hub collar 38 (see FIG. 1) to securely attach the adaptor 22 to the catheter hub 30.

Interengaging structure (not shown) between the clip support element and the clip 34 permits the clip 34 to slide in the proximal direction, but prevents the clip 34 from sliding in the distal direction. The interengaging element desirably comprises a series of ratchet teeth (not shown) disposed up on upper surface of the clip support element and a pawl (not shown) connected to the clip 34. The pawl extends from the clip 34 in a cantilever fashion and engages the ratchet teeth to prevent distal movement of the clip, as discussed in detail in U.S. Pat. No. 5,193,273, which has been incorporated by reference.

The tubular body 25, the support arm 32 and the clip support element are preferably integrally formed of molded plastic, such as, for example, a clear polycarbonate, so as to be generally stiff, but somewhat flexible. The support arm 32 desirably has enough elasticity to bend. Depressing the proximal end of the clip 34 towards the tubular body 25 moves the latch 36 of the clip 34 away from the tubular body 25. In this manner, the clip 34 pivots about the tubular body 25.

With reference again to FIG. 2, the clip support element desirably comprises a protuberance 40 positioned on an inner surface 42 of the clip support element, proximate to the proximal end of the clip 34. The protuberance is spaced from the support arm by a distance L. The protuberance 40 prevents the clip 34 from pivoting when secured by the retainer 20, as discussed below in detail. The protuberance 40 also limits the degree of deflection of the support arm 32 to reduce fatigue, as fully explained in U.S. Pat. No. 5,193,273, which has been incorporated by reference.

Retainer for Catheter Adaptor

FIGS. 3 through 5 illustrate the retainer 20. The retainer 20 has a generally parallelepiped shape defining a central channel 44 interposed between a pair of opposing longitudinal walls 46. The central channel 44 extends through the retainer 20 along an axis which is generally parallel to the longitudinal axis of the retainer.

As best seen in FIG. 4, the central channel 44 has a generally circular cross-sectional shape which is truncated at a upper end to form a generally U-shaped channel having an upper opening 47. The central channel 44 has a diameter sized to receive the tubular body 25 of the catheter adaptor 22. In a preferred embodiment, the diameter of the central channel 44 generally matches that of the tubular body 25 or is slightly larger.

In cross-section, the central channel 44 extends through an arc greater than 180N about the channel axis such that the transverse length of the opening 47 is less than the diameter of the central channel 44. In an exemplary embodiment, the central channel 44 extends through an arc of about 200N about the channel axis.

FIG. 5 illustrates the channel axis which is desirably skewed relative to a base surface 48 of the retainer 20. An incident angle θ formed between the base surface 48 and the channel axis is less than 45N. The incident angle θ desirably ranges between 0N and 30N. In an exemplary embodiment for intravenous use, the angle θ preferably equals approximately 7N. In another exemplary embodiment for arterial use, the incident angle θ preferably equals about 22N. In a further exemplary embodiment, for peripherally inserted central catheters (PICC), the incident angle θ preferably equals 0N.

The longitudinal walls 46 are substantially identical. Each wall 46 has a thickness measured in the lateral direction less than the length of the support arm 32. The wall 46 is thus interposed between the tubular body 25 and the clip 34 when the tubular body 25 is inserted into the central channel 44. The length of each wall 46, measured in the longitudinal direction, is preferably coextensive with the length of the retainer 20.

Each wall 46 comprises a uniform series of slots 50. The series comprises at least two (2) slots 50, and not more than twenty (20) slots 50. More preferably, the series comprises less than seven (7) slots 50. In an exemplary embodiment, as illustrated in the figures of the application, the series comprises four (4) slots 50.

Each slot 50 is sized to receive the support arm 32 of the catheter adaptor 22 to prevent longitudinal displacement of the adaptor 22, as discussed in detail below. Each slot 50 desirably has a rectangular shape. As seen in FIG. 3, the slots 50 extend from an exterior surface 52 through the wall 44, and open into the central channel 44. The width of each slot 50 (measured longitudinally) is desirably slightly greater than the width of the support arm 32, measured in the longitudinal direction to receive the support arm 32, as discussed below.

As illustrated by FIG. 5, each slot 50 has a height as measured in the transverse direction between an upper edge 54 of the longitudinal wall 46 and the bottom 56 of the central channel 44. The height of the slot 50 desirably equals approximately the width of the support arm 32 such that the support arm 32 does not protrude from the retainer 20 in the transverse direction.

The spacing S between the slots 50, on center, desirably equals about half the distance L (see FIG. 2) between the support arm 32 and the protuberance 40 of the catheter adaptor 22.

As FIG. 3 illustrates, a distance X between the most distal slot 50 and the distal end of the retainer 20 is less than the longitudinal distance Y (see FIG. 2) between the support arm 32 and the latch 36 positioned in its most proximal position. This spacing enables the support arm 32 to rest in the most distal slot 50 with the latch 36 retaining a catheter hub 30 distal of the retainer distal end.

FIG. 5 illustrates the upper edge 50 of the longitudinal wall 46 which comprises a series of chamfers 58, each of which slopes into a slot 50. That is, the portion of upper edge 50 of the longitudinal wall 46 which surrounds a slot 50 includes a pair of chamfers 58, with one chamfer 58 located on either side of the slot 50. The chamfers 58 slope downward toward the slot 50 to facilitate the insertion of the support arm 32 of the catheter adaptor 22 into the slot 50, as discussed below.

As shown by FIGS. 3 and 5, each longitudinal wall 46 further comprises a relief 60 disposed on the proximal end of the retainer 20. The relief 60 is sized to receive the protuberance 40 of the adaptor 22. The depth of the relief 60 measured in the lateral direction desirably is slightly greater than the height of the protuberance 40 (i.e., the distance by which the protuberance protrudes from the inner surface 42).

The relief 60 is spaced in the longitudinal direction from the most proximal slot 50 by a distance approximately equal to the spacing S between the slots 50. Thus, the protuberance 40 rests in the relief 60 with the support arm 32 positioned in either of the two most proximal slots 50, as discussed in detail below.

FIGS. 3 and 4 illustrate a key-way groove 62 of the retainer 20. The key-way groove 62 facilitates the removal of the catheter adaptor 22 from the retainer 20, as discussed below in detail. The key-way groove 62 lies at the proximal end of the retainer 20. The key-way groove 62 extends into the retainer 20, and toward the retainer base surface 48 from the bottom surface 56 of the central channel 44. The key-way groove 62 has a transverse width less than the diameter of the central channel 44, and more preferably has a width approximately equal to two-thirds the diameter of the central channel 44. The longitudinal length of the key-way groove 62 desirably equals approximately the longitudinal length of the recesses 60 in the longitudinal walls 46.

The retainer 20 is made of relatively stiff plastic material (e.g., polycarbonate), but is somewhat flexible such that the adaptor 22 forces the upper edges 54 of the longitudinal walls 46 outwardly when a nurse presses the adaptor 24 into the central channel 44 of the retainer 20. When the adaptor 22 sits in the central channel 44, the upper edges 54 of the walls 46 snap inwardly to their original position to securely hold the adaptor 22 within the retainer 20.

An adhesive attaches the retainer 20 to base pad 16. Alternatively, the retainer 20 may be attached to the base pad 16 by like means (e.g., embedding or otherwise weaving the retainer 20 into the base pad 16) as well.

Base Pad

As illustrated by FIG. 1, the flexible base pad 16 comprises a laminate structure comprising an upper paper or other woven or non-woven cloth layer 64, an inner cellulose foam layer 66, and the bottom adhesive layer 18. Alternative, the flexible base pad 16 may comprise an adhesive bottom layer and an upper cellulose foam layer. An upper surface of the foam layer is roughened by corona treating the foam with a low electric charge, as known in the art. The roughened or porous upper surface of the base pad 16 improves cyanoacrylate (or other types of adhesive) adhesion when attaching the retainer 20 to the pad 16.

A removable paper or plastic backing (not shown) desirably covers the bottom adhesive layer 18 before use. The backing preferably resists tearing and is divided into a plurality of pieces to ease attachment of the pad 16 to the patient's skin, as explained below. Desirably, the backing is split along the center line of the flexible base pad 16 in order to expose only half of the adhesive bottom surface 18 at one time. The backing also advantageously extends beyond at least one edge of the base pad 16 to ease removal of the backing from the adhesive layer 18.

As seen in FIG. 2, one or more tabs 67 may be attached to a portion of the backing which extends beyond the flexible base pad 16. In an exemplary embodiment, the tabs 67 have the same laminate structure as the flexible base pad 16. The tabs 67 also can be formed by the paper backing extending beyond the edge of the base pad 16. The tab 67 may also include indicia 69 in the form of dots, words, figures or the like to indicate the placement of fingers when removing the backing from the base pad 16.

A nurse grips the tab 67, preferably at the location of the indicia 69, and peels the backing off one half of the bottom adhesive layer 18. The nurse then places the bottom layer 18 against the patient's skin to adhere the base pad 16 to the patient. Light pressure over the upper layer 64 assures good adhesion between the base pad 16 and the patient's skin. The base pad 16, due to its flexibility, conforms to the contours of the topical surface to which the base pad 16 adheres. The nurse then repeats this procedure for the other half of the pad 16. Alternatively, the nurse may completely remove the backing from the pad 16 before attaching the pad 16 to the patient's skin.

The base pad 16 desirably comprises a notch 68 positioned distal of the location of the retainer 20 on the pad 16 and adjacent to the point of insertion of the catheter cannula. The notch 68 is sized to permit visual inspection of the catheterized site.

As seen in FIG. 2, the base pad 16 desirably may comprise indicia 70 in the form of an arrow which indicates the proper orientation of the base pad 16 in reference to catheterized site. Although the figures illustrate the indicia in the form of an arrow, it is contemplated that other forms of indicia, such as, for example, words or other graphics, could be used as well. In proper use, as illustrated in FIG. 1, the indicia 70 should point in the proximal direction, towards the indwelling catheter 14, or otherwise indicate the proper locate of the pad 16 in reference to the indwelling catheter 14.

In an exemplary embodiment, the laminate structure of the base pad is preferably formed by rolling a paper tape, such as a micro-porous rayon tape, available commercially as MICRO-PORE tape from 3M (Item No. 1530), over a medical grade polyvinyl chloride foam tape, such as that available commercially from 3M (Item No. 9777L). The foam tape preferably includes the bottom liner or backing. The base pad 16 and the tabs 67 are then stamped out of the laminated sheet of foam and paper. The backing between the tabs and the base pad, however, is desirably not severed such that the tabs 67 remain attached to the backing covering the adhesive section 18 of the base pad 16. The backing is then cut into two pieces along the center line of the pad 16 and between the tabs 67.

Tube Clip

FIGS. 1 and 2 illustrate the tube clip 24. The clip 24 secures the fluid supply tube 12 to form a safety loop, as known in the art.

Figure 6:
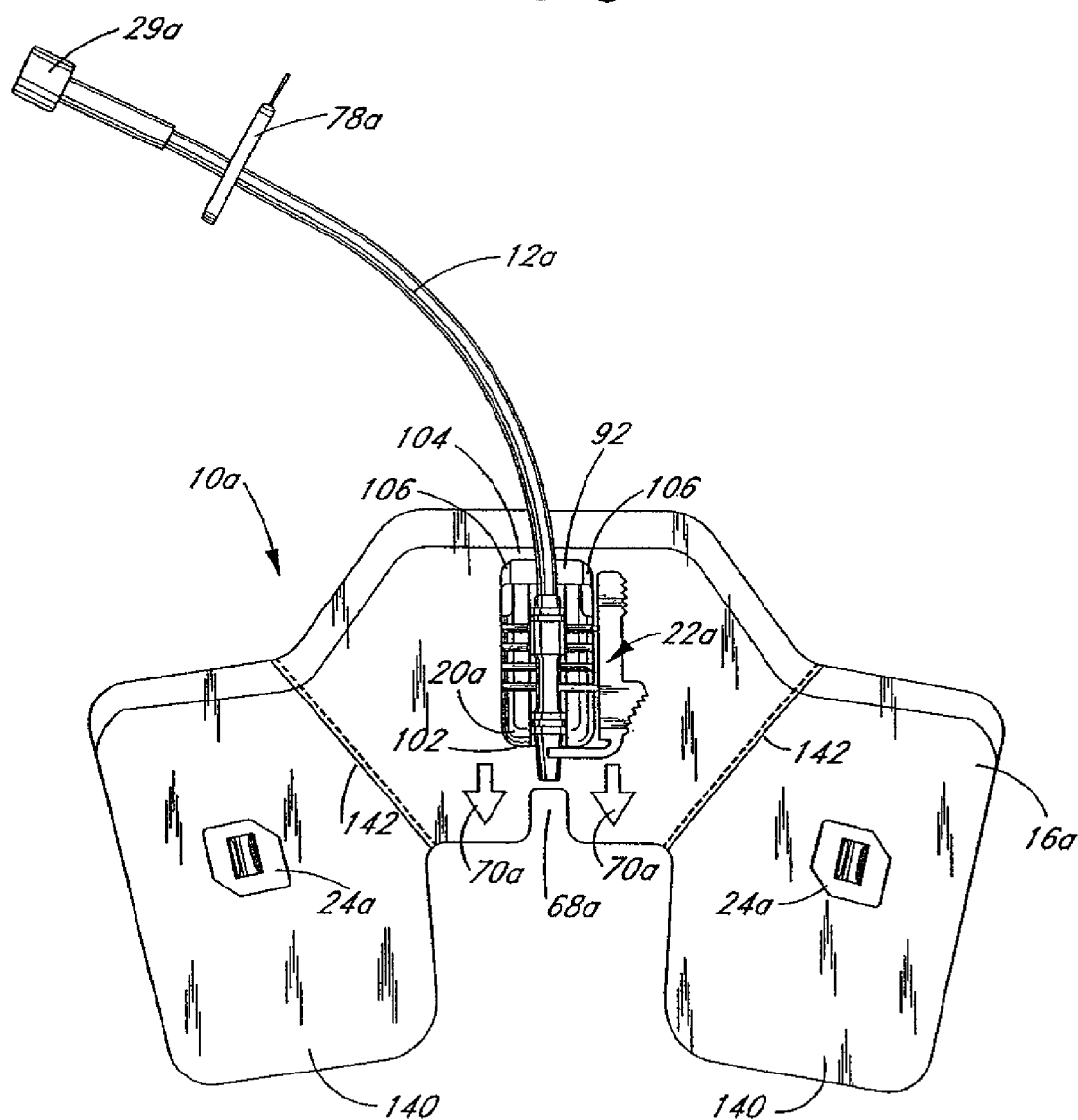
FIG. 6 is a top plan view of a catheter anchoring system in accordance with another preferred embodiment of the present invention.

The tube clip has a plate-like base 72 adhered to or embedded in the base pad 16. The tube clip 24 may be located on the base pad 16 on either side of the retainer 20 to accommodate left hand or right hand mounting. As illustrated in FIG. 6, the anchoring system 10 may further include a second tube clip 24 located on the other side of the retainer 20 from the first tube clip 24.

The clip 24 defines a channel 74 having a generally circular cross-sectional configuration truncated to form an upper orifice 76. The diameter of the channel 74 is desirably slightly less than that of the fluid supply tube 12 so as to ensure a secure interconnection. The channel 74 receives a portion of the fluid supply tube 12 through the orifice 76 upon application of gentle pressure or by pulling the tubing 12 across and through the orifice 76 of the tube clip 24, as explained below. The clip 24 surrounds a substantial portion of the tubing 12 with the tubing 12 positioned within the channel 74.

As seen in FIG. 2, the upper edge of the channel includes tapered ends 77 at the proximal and distal ends of the clip 24. Each tapered end 77 forms a smooth transition between the side edge of the channel 74 and the upper edge, and tapers in lateral width from the side edge toward the center of the tube clip 24. The tapered ends 77 help guide the fluid supply tube 12 into the channel 74 when a nurse pulls the tube across the clip 24. Thus, the nurse does not have to pinch the tube 12 to insert it into the clip 24. Also, the nurse's gloves do not get stuck in the clip 24 when inserting the tube 12, as is typically the case where the nurse is required to pinch the tube 12 to insert it into the clip 24.

Slide Clamp

As illustrated in FIGS. 1 and 2, the catheter anchoring system 10 desirably additionally includes a slide clamp 78 to regulating fluid flow through the tubing, as known in the art. The clamp 78, at one end, includes an aperture 80 which receives the fluid supply tube 12, and, at the opposite end, includes a tab 82. The clamp 78 has a generally forked shape formed by a pair of prongs 84 which defines the aperture 80. The tube 12 snaps between the prongs 84 and into the aperture 80, which has a diameter slightly larger that the fluid supply tube 12.

The prongs 84 converge together in the direction towards the tab 82 to form a tapering slot 86 which opens into the aperture 80. The prongs 84 pinch the tube 12 closed with the tube 12 positioned in the slot 86 so as to block fluid flow therethrough. The clamp 78, however, slides over the tube 12 with the tube 12 positioned through the aperture 80.

The tab 82 desirably has a rectangular shape which generally corresponds the to shape of the key-way groove 62 of the retainer 20. The tab 82 preferably has a thickness greater than that of the distal end of key-way groove 62, measured in the transverse direction, so as to pry the adaptor 22 from the retainer 20. As explained in detail below, the tab 82 may be used to remove the catheter adaptor 22 from the retainer 20.

Retainer Location Adjustment Mechanism

Figure 8:
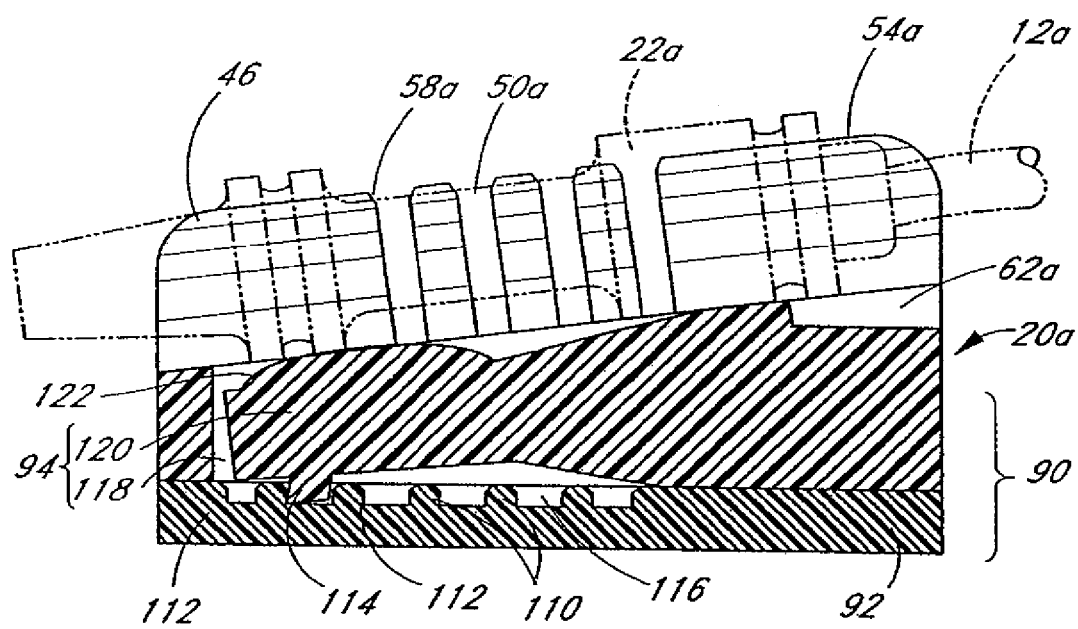

FIG. 6 through 8 illustrate a catheter anchoring system 10a in accordance with another preferred embodiment of the present invention. Where appropriate, like numbers with an "a" suffix have been used to indicate like parts of the two embodiments for ease of understanding.

The catheter anchoring system 10a is substantially identical to the above-described anchoring system 10, with the addition of a retainer location adjustment mechanism 90.

As best seen in FIG. 8, the location adjustment mechanism 90 comprises a base 92 and interlocking mechanism 94 which interconnects the base 92 and the retainer 20a. The retainer 20a slides over the base 92 and the interlocking mechanism 94 secures the retainer 20a to the base 92 at various longitudinal positions. The adjustment mechanism thus allows for precise positioning of the retainer 20 relative to the catheter 14 after the pad 16 is attached to the patient's skin.

The base 92 has a generally parallelepiped shape and comprises a rail 96. FIG. 7a best illustrates that the rail 96 desirably has a "dove-tail" configuration in cross section. That is, the rail 96 has a cross-sectional shape with a flat upper edge 98 and a pair of opposing side edges 100, each edge 100 being angled inward from the upper edge 98 toward the middle of the rail 96. The rail 96 extends along the longitudinal length of the base 92 from the distal end 102 of the base 92 to a point just short of the base proximal end 104. The base 92 includes a pair of stops 106 at the proximal end 104 which close off the proximal end of the rail 96.

An adhesive attaches the base 92 to base pad 16a. Alternatively, the base 92 may be attached to the base pad 16a by like means (e.g., embedding or otherwise weaving the base 92 into the base pad 16a) as well.

The retainer 20a, configured in accordance with the above-description, additionally comprises a groove 108 having a cross-sectional shape corresponding to that of the rail 96. The retainer groove 108 receives the base rail 96 in a manner permitting the retainer 20a to slide over the base 92, but preventing the retainer 20a from moving in the transverse direction away from the base 92. The base stops 106 also limit the retainer's longitudinal travel in a proximal direction.

The interlocking mechanism 94 comprises a plurality of teeth 110 disposed on an upper surface 112 of the base 92, and a pawl 114 connected to the retainer 20a. The teeth 110 desirably have generally rectangular cross-sectional shapes, and lie in seriatim along the longitudinal axis of the base 92. The upper edge of each tooth 110 includes a chamfer 112 to facilitate the engagement of the pawl 114 with a hollow 116 formed between adjacent teeth 110, as discussed below. The longitudinal length of each tooth 110 desirably extends generally normal to the longitudinal axis of the base 92.

The pawl 114 has a shape configured to insert into and engage with the hollow 116 defined between the teeth 110. The pawl 114 preferably has a width, measured in the longitudinal direction, slightly less than that of the hollow 116.

The retainer 20a comprises an aperture 118 extending between the retainer base surface 48a and the channel bottom surface 56a. A flexible finger 120 extends from the retainer 20a in a cantilever fashion and into the retainer aperture 118. The flexible finger 120 supports the pawl 114 at its distal end. Although FIG. 8 illustrates the finger 120 as extending in the distal direction, it is contemplated that the finger 120 can alternatively extend in the proximal direction as well.

The flexible finger 120 preferably comprises a protuberance 122 which extends upwardly beyond the channel bottom surface 56a and into the central channel 44a with the finger 120 in an undeflected state. The cantilever nature of the finger 120 enables the finger 120 to deflect downward so that the protuberance 122 lies below the retainer bottom surface 56a. With the finger 120 so deflected, the pawl 114 engages the series of teeth 110. That is, the pawl 114 inserts into a hollow 116 defined between the teeth 110. The interengagement between pawl 114 and the teeth 110 prevents the retainer 20a from sliding over the base 92.

S-Clip

Figure 10:
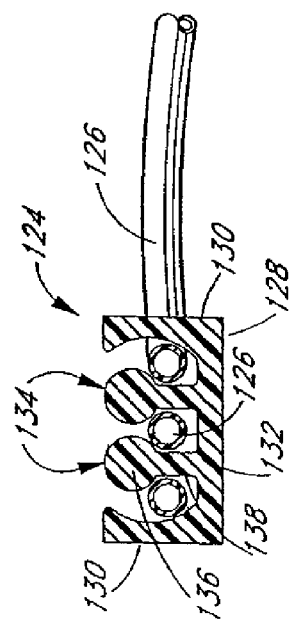
FIG. 10 is a side elevational view of an S-clip of the catheter anchoring system of FIG. 9 taken along line 10-10.
Figure 9:
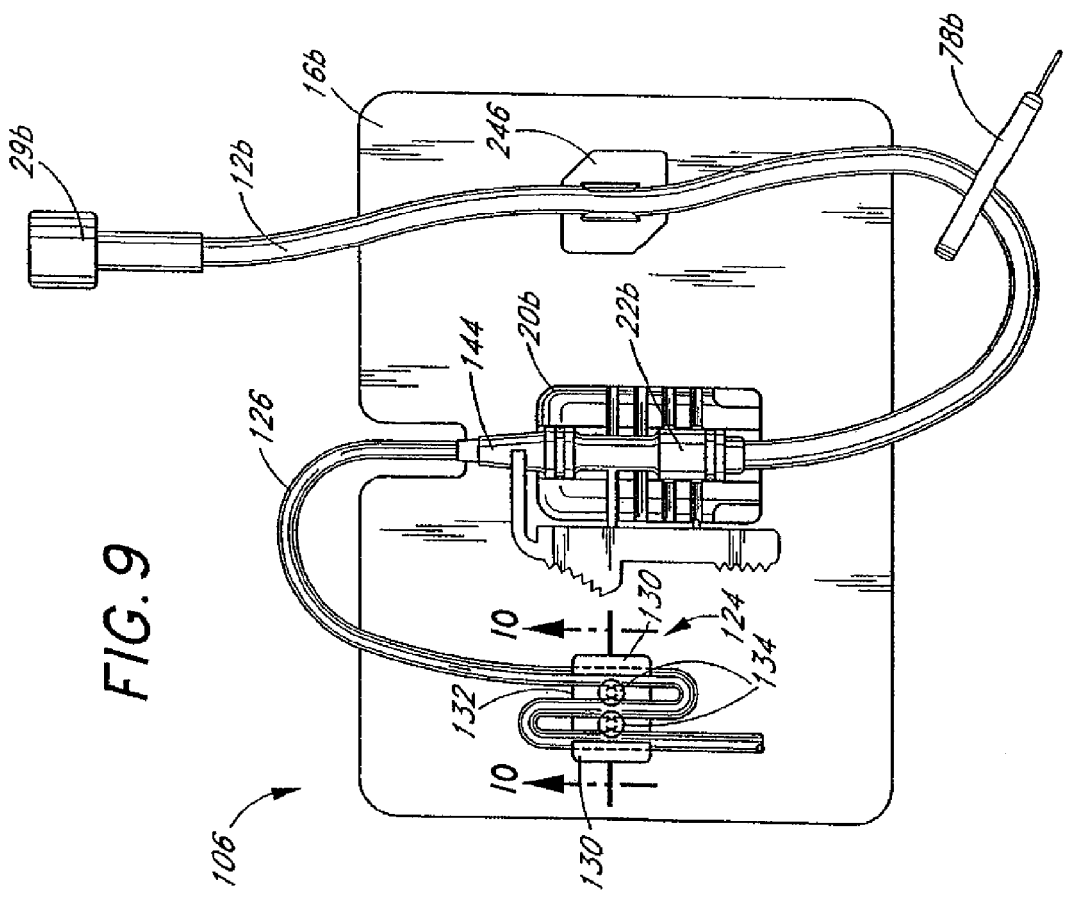
FIG. 9 is a top plan view of a catheter anchoring system in accordance with an additional preferred embodiment of the present invention.

FIGS. 9 and 10 illustrate a catheter anchoring system 10b in accordance with a further embodiment of the present invention. Where appropriate, like numbers with an "b" suffix have been used to indicate like parts of the embodiments for ease of understanding.

The catheter anchoring system 10b is substantially identical to the anchoring system 10 first described above, with the addition of an S-clip 124 to retain a microbore or small bore tubing 126. The microbore tubing is commonly used, for example, with epidural catheterization procedures, as discussed in detail below.

The S-clip 124 comprises a generally U-shaped channel 128 defined by a pair of arcuate, upstanding walls 130 extending from a base plate 132. As best seen in FIG. 10, the S-clip 124 further comprises a plurality of retainers 134, each retainer 134 having a spherical head 136 support by a cylindrical stem 138. The stems 138 extend from the base plate 132. The retainer stems 138 are positioned from one another and from the upstanding walls 130 by a distance slightly greater than the diameter of the microbore tubing 126. The retainers 134 are also positioned such that the spherical heads 136 of the retainers 134 are positioned from one another and from the upstanding walls 130 by a distance slightly less than the microbore tubing 126. As best seen in FIG. 10, the retainer heads 136 prevent the microbore tubing 126 from disengaging from the S-clip 124 in the transverse direction once the microbore tubing 126 is snaked between the retainers 134 and the upstanding walls 130.

An adhesive attaches the base plate 132 of the S-clip 124 to base pad 16b. Alternatively, the base plate 132 may be attached to the base pad 16b by like means (e.g., embedding or otherwise weaving the base plate 132 into the base pad 16b) as well.

The components of the anchoring system 10, save the base pad 16 (i.e., the retainer 20, tube clip 24, adaptor 22, slide clamp 78, base 92 and S-clip 124), may be constructed in any of a variety of ways which will be well known to one of skill in the art. For instance, each individual component may be integrally molded such as by injection molding or by thermoplasty. The components preferably comprise a durably, flexible material, and more preferably comprise a generally inert, non-toxic material. In a preferred embodiment, the components are molded of plastic, such as, for example, polycarbonate, polyvinylchloride, polypropylene, polyurethane, tetrafluoroethylene (e.g., TEFLON7), polytetrafluoroethylene (a.k.a., PTEF), acetal resin (e.g., DELRIN7), chlorotrifluoroethylene (e.g., KEL-F7), nylon or like polymers.

Method of Use

The following discussion of the method of use will be with reference to FIGS. 1 and 2, and initially will be in the context of intravenous catheterization. As the following discussion will illustrate, however, it is understood that the anchoring system 10 can be used in other catheterization procedures as well. The discussion of the method of use is intended to augment the above description of the invention, and, thus, should be read together.

A nurse typically begins the catheterization process by positioning the catheter 14 at a desired location above a vein. The nurse introduces a needle or other stylus through a cannula portion of the catheter 14 and into the skin of the patient at a desired angle of incident. For intravenous use, the catheter 14 commonly has an incident angle of approximately 7N. The nurse then inserts the cannula of the catheter 14 into the patient and withdraws the needle or stylus. The catheter hub 30 remains exposed above the skin.

The nurse inserts the distal end of the adaptor 26 into the catheter hub 30. The clip 34 has been slidably mounted in a most distal position so that it does not interfere with the insertion of the adaptor distal end 26 into the catheter hub 30.

The nurse then slides the clip 34 in a proximal direction to engage the catheter hub 30. In this manually selected position, the clip 34 securely attaches the adaptor 22 to the catheter 14. The ratchet teeth of the adaptor 22 cooperate with the pawl to resist distal movement of the clip 34 and to hold the clip 34 in the manually selected position.

The nurse removes the paper backing which initially covers the adhesive bottom surface 18 of the base pad 16, and attaches the pad 16 to the patient's skin proximate to the indwelling catheter 14. Specifically, the nurse grips the backing tab 67 proximate to the retainer 20. The indicia 69 on the tab 67 indicates the locate at which the nurse should grip the tab 67. The nurse then pulls on the tab 67 and peels the backing off one half of the bottom adhesive layer 18. The nurse positions the slot 68 of the pad 16 around the catheter cannula 14 with the instructing indicia 70 (e.g., indicating arrow) pointing in the direction of the catheter 14. The nurse then places the bottom layer 18 against the patient's skin to adhere the base pad 16 to the patient. Light pressure over the upper layer 64 assures good adhesion between the base pad 16 and the patient's skin. The base pad 16, due to its flexibility, conforms to the contours of the topical surface to which the base pad 16 adheres.

The nurse then repeats this procedure for the other half of the pad 16. Alternatively, the nurse may completely remove the backing from the pad 16 before attaching the pad 16 to the patient's skin.

The nurse orients the adaptor 22 with the clip 34 positioned to the side of the tubular body 25 (i.e., with the support arm 32 extending in the lateral direction) and locates the adaptor support arm 32 above the series of retainer slots 50 with the latch 36 positioned distal of the retainer distal end.

The nurse then snaps the adaptor 22 into the retainer 20 located proximal of the pad notch 68. In doing so, the adaptor 22 is pressed between the longitudinal walls 46 of the retainer 20 with the support arm 32 extending in a lateral direction. As the nurse presses the adaptor 22 into the retainer 20, the chamfered edges 58 around the slots 50 of the longitudinal wall 46 guide the support arm 32 into one of the slots 50.

As mentioned above, the opening 47 of the channel 46 has a smaller width measured in the lateral direction than the diameter of the tubular body 25. The lateral walls 46 thus deflect outwardly in a lateral direction. Once the tubular body 25 of the adaptor 22 rests within the central channel 44 of the retainer 20, the lateral walls 46 spring back to snap the adaptor 22 in place. The walls 46 of the retainer 20 thus prevent unintentional transverse and lateral movement of the adaptor 22.

In this position, the protuberance 40 of the adaptor 22 either rests either in a slot 50 or in the relief 60, proximal of the slot 50 through which the support arm 32 passes. The protuberance 40 engages a portion of the longitudinal wall 46, which forms either the relief 60 or the slot 50, to prevent the clip 34 from pivoting relative to the tubular body 25. The protuberance 40 thus ensures that the latch 36 maintains engagement with the catheter hub 30.

The slot 50 through which the support arm 32 passes prevents the adaptor 22 from sliding in the longitudinal direction. That is, the slot 50 prevents longitudinal displacement of the adaptor 22 when secured within the central channel 44.

The ergonomic design of the retainer 20 provides for a variety of positions of the adaptor 22 in the retainer 20 so that the retainer 22 is not technique or position sensitive. That is, a nurse can simply press the adaptor 22 into the retainer 20, irrespective of the side on which the support arm 32 is located, and irrespective of the position of the support arm 32 relative to a particular slot 50. So long as the support arm 32 is positioned above the series of slots 50, the chamfered edges 58 of the wall 46 will guide the support arm 32 into a slot 50. The protuberance 40 of the adaptor 22 also fits within an adjacent slot 50 or the relief 60.

With the support arm 32 extending through a slot 50 of the retainer 20, the adaptor 22 lies in a "low profile" position. That is, the support arm 32 of the adaptor 22 extends in the lateral direction to reduce the overall height of the anchoring system 10, as measured in the transverse direction. This position of the adaptor 22 reduces the risk of the system 10 interfering with surrounding action. The retainer 20, however, allows the adaptor 22 to rotate either to a position in which the support arm 32 extends in the transverse direction, or to a position 180N for the original position to locate the adaptor clip 34 on the opposite side of the retainer 20.

Once in the low profile position, the adaptor 22 will normally remain in this position until the adaptor 22 and its associated tubing 12 are removed and replaced by another.

As FIG. 1 illustrates, the nurse may also form a safety loop in the fluid supply tubing 12, as known in the art, and secure the safety loop to the patient by inserting a portion of the tubing 12 into the tube clip 24. The safety loop absorbs any tension applied to the fluid supply tube to prevent the adaptor 22 and/or catheter 14 from being pulled.

A nurse may use the slide clamp 78 to remove the adaptor body 25 from the retainer 20. The nurse inserts the tab 82 of the slide clamp 78 into the key-way groove 62 on the proximal end of the retainer 20. Because the tab 82 has a larger width than the depth of the key-way groove 62, measured in the transverse direction, the tab 62 pries the tubular body 25 from the central channel 44 as the nurse inserts the tab 82 into the key-way groove 62 in the distal direction. The nurse may further use the slide clamp 78 to leverage the proximal end of the tubular body 25 out the upper opening 47 of the retainer 20. Having displaced the proximal end of the adaptor 22 from the retainer 20, the nurse may easily remove the adaptor distal end from of the retainer 20. Alternatively, the nurse may also remove the tubular body 25 by lifting up on the tubing 12 while holding down the pad 16 or the retainer 20 with the other hand.

FIGS. 6 through 8 illustrate the catheter anchoring system 10a particularly suited for arterial catheterization. Because of the criticality of the incident angle (i.e., the angle at which the catheter 14a projects into the patient) at which the catheter 14a must be maintained, it is advantageous to precisely position the retainer 20a so that the retainer 20a holds the catheter 14a at the desired incident angle. The desired range of incident angle commonly is about 5N-30N for arterial catheterization. The incident angle preferably ranges between about 15N and about 25N, and more preferably equals about 22N.

A nurse inserts the catheter cannula 14a into an artery in a similar manner to that described above in connection with intravenous catheterization. The nurse subsequently connects the adaptor 22a to the indwelling catheter 14a as previously described. The nurse also attaches the flexible pad 16a to the patient in a like manner to that described above. If desired, the nurse can remove one of the wings 140 of the pad 16a before attaching the pad 16a to the patient, by tearing the pad 16a along the perforation line 142.

The nurse orients the adaptor 22a with the clip 34a positioned to the side of the tubular body 25a (i.e., with the support arm 32a extending in the lateral direction) and locates the adaptor support arm 32a above the series of retainer slots 50a with the latch 36a positioned distal of the retainer distal end. If the nurse positions pad 16a too close to or too far from the indwelling catheter 14a, the nurse can slide the retainer 20a in the desired direction to locate the retainer slots 50a beneath the adaptor support arm 32a.

The nurse then snaps the adaptor 22a into the retainer 20a located proximal of the pad notch 68a. In doing so, the chamfered edges 58a around the slots 50a of the longitudinal wall 46a guide the support arm 32a into one of the slots 50a. The retainer 20a automatically slides longitudinally to precisely position a corresponding slot 50a beneath the support arm 32a. The adaptor 22a thus snaps into the retainer 20a without causing the catheter 14a to move substantially.

The tubular body 25a contacts the protuberance 122 of the finger 120 and causes the finger 120 to deflect downward as the adaptor tubular body 25a snaps into the central channel 44a. In turn, the pawl 114 engages the series of teeth 110 which prevents longitudinal movement of the retainer 20a while holding the adaptor 20a. If the nurse removes the adaptor 22a—preferably by using the slide clamp tab 82a—the finger 120 springs back to its undeflected state and the retainer 20a freely slides over the rail 96. The pawl 114 normally does not engage the series of teeth 110.

The ability to precisely position the retainer 20a beneath the catheter adaptor 22a connected to the catheter 14a, enables the nurse to hold the catheter 14a in a stable position and ensures that the retainer 20a will hold the adaptor 22a, and thus the catheter 14a, at the precise incident angle. Without the ability to adjust the longitudinal position of the retainer 20a, the nurse may perform a series of position iterations before properly locating base pad 16a, and thus the retainer 20a, relative to the indwelling catheter 14a.

For epidural catheterization, an anesthesiologist, for example, inserts the distal end of microbore tubing 126 into the epidural space. The proximal end of the microbore tubing 126 conventionally includes a Toughy-Bourst adaptor 144 or other adaptor device to couple with the fluid supply tube 12b transporting the anesthesia. It is imperative that the connection between the microbore tubing 126 and the fluid supply tubing 144 remain intact, and that the distal end of the microbore tubing 126 remains in place. For if the epidural space is exposed to air-borne microbes, meningitis may develop. Thus, a secure interconnection between the microbore tubing 126 and the fluid supply 12b should exist and the microbore tubing 126 should be isolated from any tension placed on either the fluid supply tube 12b, as well as the adaptor 22b.

FIGS. 9 and 10 illustrate the catheter anchoring system 10b particularly suited for epidural catheterization. A doctor uses the present anchoring system 10b in a manner similar to that described above in connection with intravenous catheterization, with the exceptions that doctor connects the adaptor 22b to microbore tubing 126 and adheres the base pad 16b to the patient's torso.

The doctor subsequently snakes the microbore tubing 126 through the S-clip 124 by first pressing the tubing 126 between a retainer 134 and the wall 130, and then wrapping the tubing 126 between the first and second retainers 134. Light pressure forces the tube 126 between the retainers 134. The doctor then wraps the tube 126 back between the second retainer 134 and the second wall 130, and presses the tube 126 therebetween. The S-clip 124 secures the microbore tube 126 in place and isolates the microbore tube 126 from tension placed on the adaptor 22b and/or the fluid supply tube 12b with the microbore tube 126 inserted accordingly.

Additional Embodiments

Figure 11:
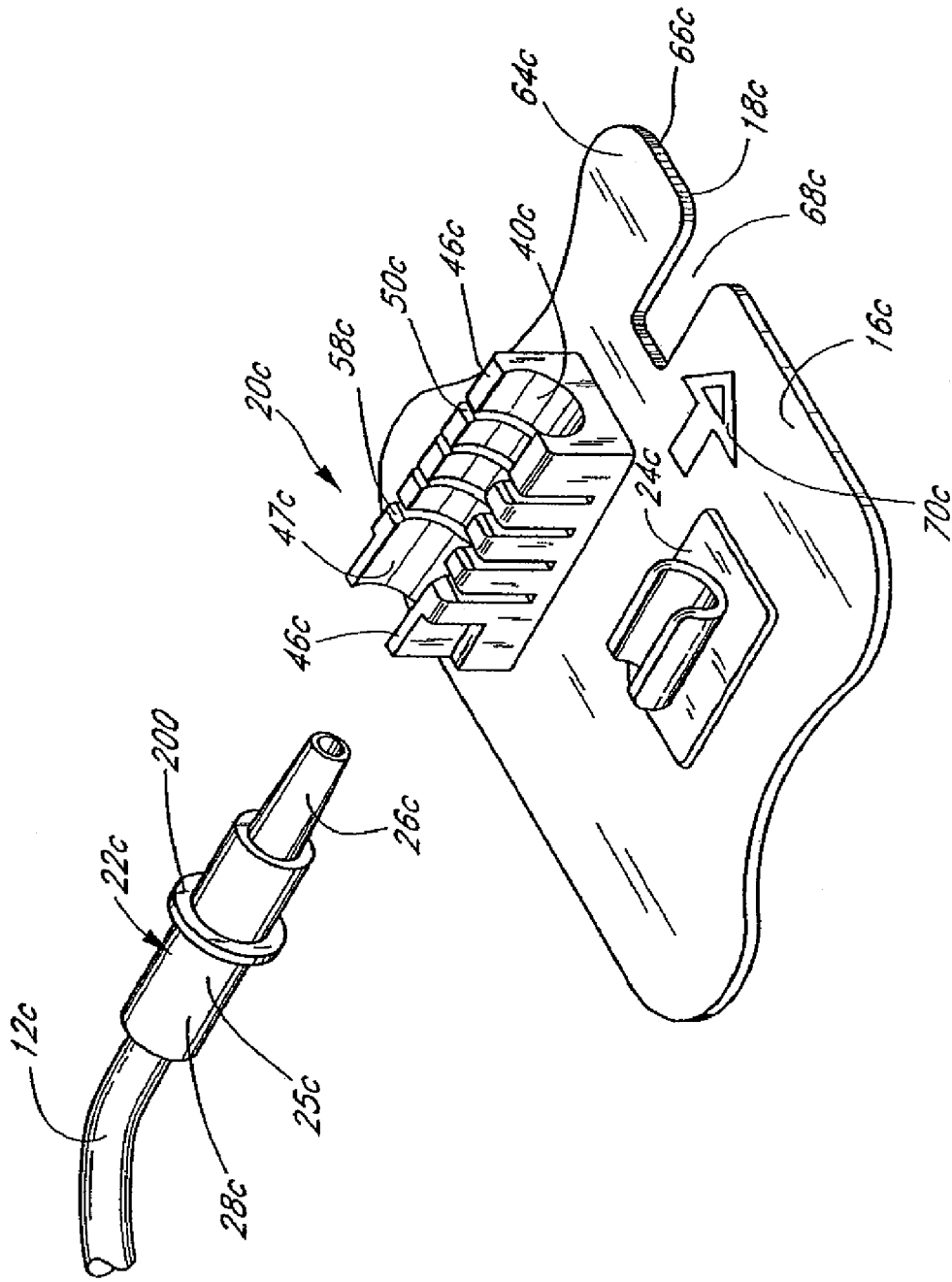
FIG. 11 is a top perspective view of a catheter anchoring system in accordance with an additional preferred embodiment of the present invention.
Figure 12:
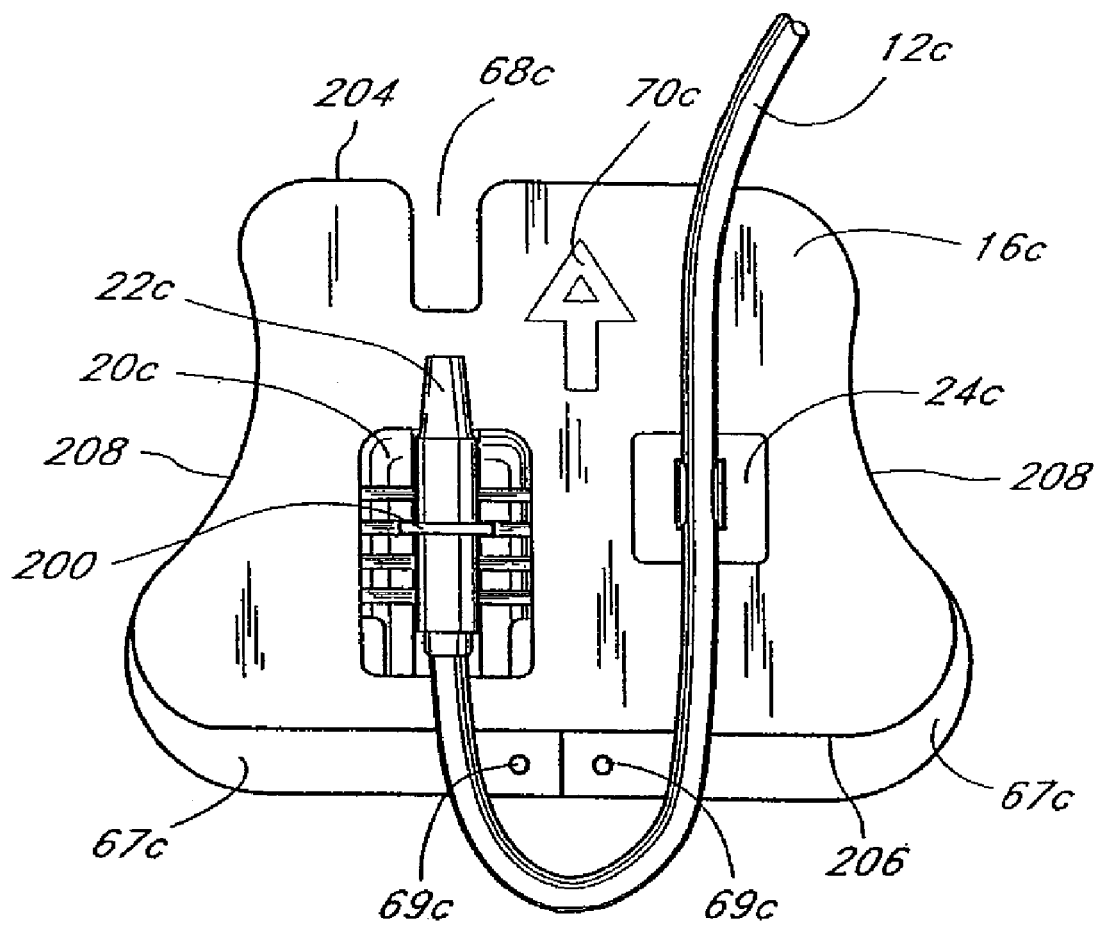
FIG. 12 is a top plan view of the catheter anchoring system of FIG. 11 illustrating an adaptor held by a retainer.

As mentioned above, it is contemplated that other types of adaptors in addition to the one disclosed above can be used as well with the present catheter anchoring system. FIGS. 11 and 12 illustrate a catheter anchoring system 10c in accordance with a further embodiment of the present invention which includes a different catheter adaptor style. Where appropriate, like numbers with a "c" suffix have been used to indicate like parts of the embodiments for ease of understanding.

Like the catheter anchoring systems described above, the present catheter anchoring system 10c principally comprises a flexible anchor pad 16c having an adhesive bottom side 18c, which attaches to the skin of the patient. The pad 16c supports a retainer 20c. The retainer 20c is configured to receive and secure in place a catheter adaptor 22c which connects to an indwelling catheter 14c. The pad 16a may also support a tube clip 24c which is used to retain a portion of the tubing 12c.

FIG. 11 illustrates the adaptor 22c as comprising a generally tubular body 25c defined between a distal end 26c and a proximal end 28c. The proximal end 28c is adapted to receive a distal end of the tube 12c. In an exemplary embodiment, at least a portion of the fluid supply tube 12c is permanently attached to the body proximal end 28c.

The distal end 26c is configured to engage a proximal end of the indwelling catheter 14c (not shown). Although FIGS. 11 and 12 illustrate the distal end 26c of the adaptor 22c as having a frusto-conical shape configured to engage a standard lure-type catheter hub 30c (not shown), it is contemplated that the distal end 26c could be configured as well to engage other types of connectors.

Figure 14:
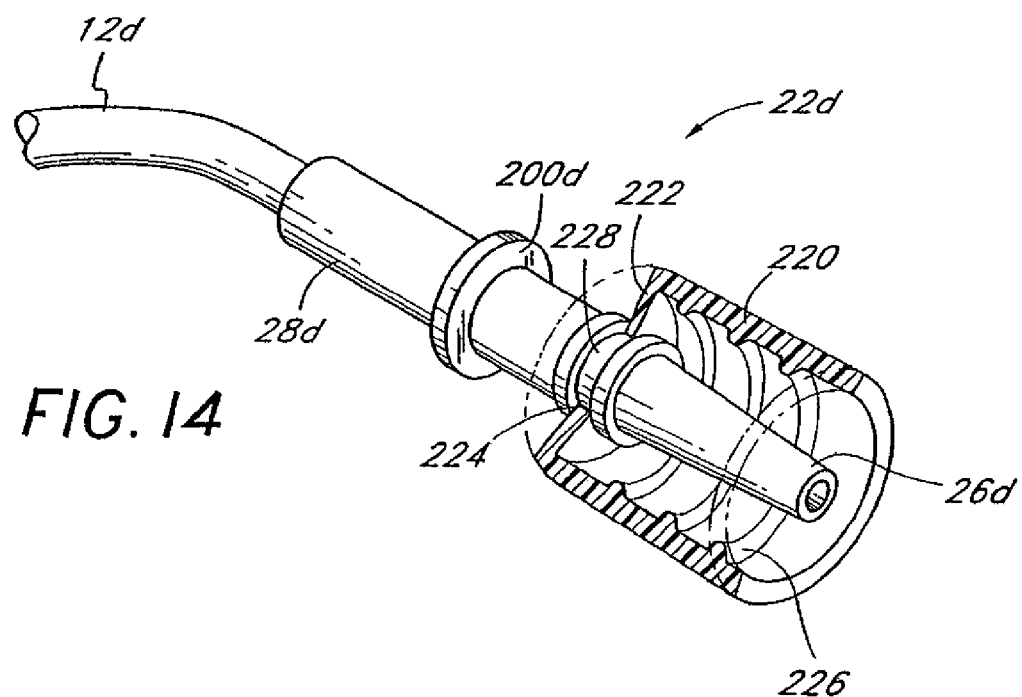
FIG. 14 is a partially sectioned perspective view of an alternative embodiment of a catheter adaptor which may be used with the anchoring system of FIG. 11.

FIG. 14 illustrates an alternative configuration of the distal end 26d of the catheter adaptor 22d. Again, for consistency, like numbers with a "d" suffix have been used to indicate like parts of the catheter adaptor of FIG. 11 and the catheter adaptor of FIG. 14.

The catheter adaptor 22d includes a standard lure-lock type fitting 220 attached to the body 25d of the catheter adaptor 22d so as to circumscribe the distal end 26d of the catheter adaptor 22d. The lure-lock fitting 220 preferably is attached in a manner which permits the fitting 220 to be rotated about the catheter adaptor body 25d. It is contemplated, however, that the distal end of the adaptor could comprise a female lure-lock type connector (i.e., a hub including nubs or threads on its external surface) as well if required by a particular application.

In the illustrated embodiment, the fitting 220 has a generally tubular shape with a closed proximal end 222. The closed end 222 includes an aperture 224 of a sufficient size to receive a portion of the adaptor body 25d, as described below. The fitting 220 includes conventional internal threads 226 in order to engage corresponding threads of a conventional female lure-lock fitting (not shown).

The adaptor body 25d desirably includes an annular groove 228 which receives a portion of the closed end 222 of the fitting 220 to interconnect the fitting 220 and the adaptor body 25d. This interconnection also permits the fitting 220 to be rotated about the adaptor body 25d.

To assemble the catheter adaptor 22d, the conical shaped distal end 26d of the body 25d is inserted into the aperture 224 of fitting closed end 222. The body 25d is then forced into the fitting 220 to slightly deflect the closed end 222 until the closed end 222 snaps into the annular groove 228 of the body 25d. In this position, the body 25d captures a portion of the fitting 220 to couple these elements together.

With reference to FIG. 11, the adaptor 22c includes at least one annular collar 200 interposed between the proximal and distal ends 28c, 26c of the tubular body 25c. The adaptor 22d of FIG. 14 also includes a like annular collar 200d. It is contemplated that the collar 200 of the adaptor 22c of FIG. 11 and the collar 200d of the adaptor 22d of FIG. 14 will be substantially identical, and, thus, the description herein will be understood as applying equally to both embodiments.

The annular collar 200 flares radially outwardly and circumscribes the tubular body 25c. The annular collar 200 has a thickness measured in a longitudinal direction which is slightly less than a width of a slot 50c in a retainer wall 46c so that the collar 200 fits within the slot 50c of a retainer wall 46c, as discussed in detail below.

The adaptor 22c is preferably formed of a durable, biocompatible plastic material. The adaptor 22c more preferably is formed of clear plastic so a nurse can see bubbles or backflow through the adaptor 22c. In an exemplary embodiment, the adaptor is formed of polycarbonate by injection molded; however, those skilled in the art will readily appreciate that the adaptor can be formed by other construction methods known in the art.

FIGS. 11 and 12 also illustrate the retainer 20c which is substantially identical to the retainer 20 described above. The retainer 20c comprises a central channel 44c interposed between a pair of opposing longitudinal walls 46c. The central channel 44c extends through the retainer 20c along an axis which is generally parallel to a longitudinal axis of the retainer 20c.

The central channel axis 44c has a generally circular cross-sectional shape which is truncated at an upper end to form an opening 47c. The central body 44c has a diameter sized to receive the tubular body 25c of the catheter adaptor 22c. In a preferred embodiment, the diameter of the central channel 44c generally matches that of the tubular body 25c.

In cross section, the central channel 44c extends through an arc greater than 180N about the channel axis such that the lateral length of the opening 47c is less than the diameter of the central channel 44c. In an exemplary embodiment, the cross-sectional shape of the central channel 44c extends through an arc of about 200N about the channel axis.

Figure 13A:
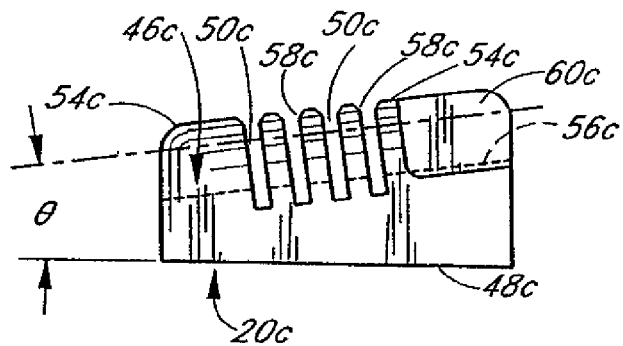
FIG. 13a is a side elevational view of the retainer of FIG. 12.

As best seen in FIG. 13a, the channel axis is desirably skewed relative to a base surface 48c of the retainer 20c. An incident angle θ formed between the base surface 48c and the channel axis is less than 45N. The incident angle θ desirably ranges between 5N and 30N. In an exemplary embodiment for intravenous use, the angle θ preferably approximately equals 7N.

The longitudinal walls 46c are substantially identical. Each wall 46c has a thickness measured in the lateral direction less than the length of the support arm 32 of the adaptor 22, as it is desirable for the present retainer 20c to accept both the above-described adaptor 22 which comprises a support arm 32 connected to a clip 34, as well as the present adaptor 22c which comprises an annular collar 200. Preferably, the thickness of the wall 46c measured in the lateral direction is greater than the distance measured radially by which the collar 200 extends beyond the exterior surface of the tubular body 25c (i.e., a radial height). The length of each wall 46c, as measured in the longitudinal direction, is preferably coextensive with the length of the retainer 20c.

Each wall 46c comprises a uniform series of slot 50c. The series comprises at least two (2) slots 50c and not more than twenty (20) slots 50c. More preferably, the series comprises less than seven (7) slots 50c. In an exemplary embodiment, as illustrated in the figures, the series comprises four (4) slots 50c.

As discussed above, each slot 50c is sized to receive the collar 200 of the adaptor 22c, as well as the support arm 32 of the catheter adaptor 22, to prevent longitudinal displacement of the respective adaptor 22, 22c. Each slot 50c desirably has a rectangular shape. As seen in FIG. 12, the slots 50c extend from an exterior surface 52c, through the wall 46c, and open into the central channel 44c. The width of the slot 50c, as measured in the longitudinal direction, is desirably slightly greater than the width of the support arm 32 and the width of the collar 200.

Figure 13B:
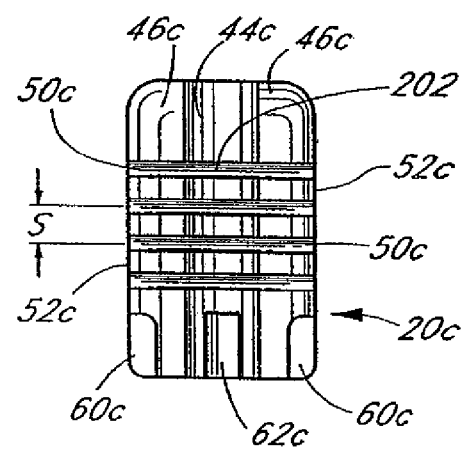
FIG. 13b is a top plan view of the retainer of FIG. 12.

As illustrated by FIG. 13a, each slot 50c extends in the transverse direction from an upper edge 54c of the longitudinal wall 46c to a point below the bottom 56c of the central channel 44c. The height of the slot 50c, as measured in the transverse direction, is thus greater than the distance between the upper edge 54c and the channel bottom 56c of the retainer 20c. As seen in FIG. 13b, the retainer 20c further includes a series of lateral grooves 202 which extend between opposing slots 50c and extend into the retainer 20c from the channel bottom surface 56c. The opposing slots 50c and groove 202 thus form a lateral channel which extends through the retainer 20c in the lateral direction and cuts into the retainer 20c from the upper edge 54c to a point below the channel bottom surface 56c. The groove 202 desirably is sized to receive a portion of the collar 200 such that with the tubular body 25c positioned within the central channel 44c, the collar 200 extends between opposing slots 50c and into the groove 202. Thus, the groove 202 has a depth, measured between the lower surface 56c of the central channel 44c and the bottom of the groove in transverse direction, which is greater than the radial height of the annular collar 200.

FIG. 13b illustrates that the spacing S between the slots 50c, on center, desirably equals about half the distal L (see FIG. 2) between the support arm 32 and the protuberance 40 of the catheter adaptor 22. The position of the slots in relation to the proximal and distal ends 26c, 28c of the retainer 20c is desirably configured in accordance with the spacing and positioning discussed above in connection with the above-described retainer 22, such that the present retainer 22c can be used with the above-described adaptor 22, including a clip 34.

FIGS. 11 and 13a illustrate the upper edge of each longitudinal wall 46c which comprises a series of chamfers 58c formed and positioned as disclosed above in connection with the retainer 20. As discussed above, the chamfers 58c slope downwardly towards the slot 50c to facilitate the insertion of either the support arm 32 of the above-described catheter adaptor 22 or the annular collar 200 of the present catheter adaptor 22c into the slot 50c.

As FIGS. 11-13b illustrate, each longitudinal wall 46c may further comprise a relief 60c disposed on the proximal end of the retainer 20c. The configuration and position of the relief 60c desirably is in accordance with the above description of the retainer 20. FIG. 11 further illustrates that the retainer 20c may additionally comprise a key-way groove 62c to facilitate removal of the catheter adaptor 22c from the retainer 20c, as discussed above. The key-way groove 62c desirably is also positioned and configured in accordance with the above disclosure in connection with the retainer 20.

The retainer 20c is made of relatively stiff plastic material, but is somewhat flexible such that the adaptor 22c forces the upper edges 54c of the longitudinal walls 46c outwardly when a nurse presses the adaptor 22c into the central channel 44c of the retainer 20c. The retainer 20c is desirably formed of polycarbonate by injection molding. When the adaptor 22c sits within the central channel 44c, the upper edges 54c of the walls 46c snap inwardly to their original position to securely hold the adaptor 22c within the retainer 20c.

An adhesive preferably attaches the retainer 20c to the anchor pad 16c. Alternatively, the retainer 20c may be attached to the anchor pad 16c by like means as well, e.g., embedding or otherwise weaving the retainer into the anchor pad 16c.

FIG. 11 illustrates the anchor pad 16c as comprising a flexible, laminate structure comprising an upper paper or other woven or non-woven cloth layer 64c and a bottom adhesive layer 18c, with an inner cellulose foam layer 66c interposed therebetween. Alternatively, the flexible base pad 16 may comprise an adhesive bottom layer 18 and an upper cellulose foam layer. An upper surface of the foam layer is roughened by corona treating with a low electric charge, as known in the art. The foam layer 66c forms a cushion between the patient's skin and the rigid, plastic retainer 20c and tube clamp 24c. The adhesive layer 18c may comprise a coating of diaphoretic or nondiaphoretic material, depending upon the patient's skin condition. A medical grade foam tape with a diaphoretic or a nondiaphoretic adhesive is available commercially from NDM Manufacturers.

The removable paper or plastic backing (not shown) desirably covers the bottom adhesive layer 18 before use. As discussed above and illustrated in FIG. 12, the backing is preferably divided into a plurality of piece and includes tabs 67c to ease removal of the backing from the pad 16. The tabs 67c may include indicia 69c (e.g., dots, text, arrows, etc.) to indicate the location at which to grip the corresponding tab 67c when peeling the removable backing off the pad 16c.

As best seen in FIG. 12, the anchor pad 16 desirably has a generally trapezoidal shape with rounded corners. A distal edge 206 of the anchor pad 16c desirably has a width, as measured in the lateral direction, wider than that of a proximal edge 204. The longer distal edge 206 provides a longer adhesive surface over a rough contact surface, such as, for example, over knuckles, vertebrae, or the like. The generally trapezoidal shape, however, minimizes the overall size of the anchor pad 16c attached to the patient. The trapezoidal shape also provides the same surface area as a square pad with a appearance of a smaller pad. The longitudinal sides 208 of the anchor pad 16c preferably taper from the proximal edge 206 to the distal edge 204, and more desirably have concave shapes.

The anchor pad includes a notch 68c positioned along the proximal edge 204 of the anchor pad 16c and adjacent to the point of insertion of the catheter cannula. Preferably, the notch 68c is symmetrically positioned about the channel axis 44c of the retainer 20c attached to the anchor pad 16c. The notch 68c is sized to permit visual inspection of the catheterized site and is large enough to allow for variable placement of the pad 16c with respect to the insertion site. That is, the notch 68c is large enough that a nurse is not required to precisely position the pad on the patient's skin with respect to the indwelling catheter 14c (not shown).

As seen in FIGS. 11 and 12, the anchor pad 16c desirably may comprise indicia 70c sometimes in the form of an arrow which indicates the proper orientation of the anchor pad 16 in reference to the catheterized site. When properly used, the indicia 70c points toward the indwelling catheter 14c (not shown).

The anchor pad 16c preferably supports a clip 24c which secures the fluid supply tube 12c to the anchor pad 16c. As seen in FIG. 12, the fluid supply tube 12c is preferably looped back around in a proximal direction and inserted into the clip 24c to form a safety loop, as known in the art. The tube clip 24c is desirably configured in accordance with the above description. The clip 24c may be made in a variety of sizes to accommodate various calibers of fluid flow tubing 12c.

In use, a nurse typically uses the catheter anchoring system 10c in connection with an indwelling catheter 14c (not shown). The catheter 14c is inserted into a body lumen, such as a vein, in accordance with the above description. The nurse then inserts the distal end 26c of the adaptor 22c into a catheter hub 30c (not shown) to connect the adaptor 22c to the catheter 14c. The nurse may then secure the adapter 22c to the catheter 14c by means of the ratchet clip, or the lure-lock fitting.

The nurse removes the paper backing which initially covers the adhesive bottom surface 18c of the anchor pad 16c, as described above, and attaches the anchor pad 16c to the patient's skin proximate to the indwelling catheter 14c. The nurse specifically positions the notch 68c of the pad 16c around the catheter cannula 14c with the indicating arrow 70c pointing in the direction of the catheter 14c. The nurse generally aligns the proximal edge 204 of the anchor pad 16c with the insertion site.

The nurse positions the adaptor 22c above the series of retainer slots 50c, and snaps the adaptor 22c into the retainer 20c. In doing so, the adaptor 22c is pressed between the longitudinal walls 46c of the retainer 20c with the annular collar 200 extending into opposing slots 50c and into the corresponding groove 202 of the retainer 20c. As the nurse presses the adaptor into the retainer 20c, the chamfered edges 58c around the slots 50c of the longitudinal walls 46c guide the annular collar 200 into the slots 50c. The retainer 20c secures the adaptor 20c as described above.

With the annular collar 200 positioned in the opposing slots 50c the adaptor 22c is prevented from sliding in a longitudinal direction.

Like the above-described embodiments of the retainer, the ergonomic design of the retainer 20c provides for various positions of the adaptor 22c in the retainer 20c so that the retainer 22c is not technique- or position-sensitive. That is, a nurse can simply press the adaptor 22c into the retainer 20c, irrespective of the position of the annular collar 20 relative to a particular slot 50c of the retainer 20c. So long as the annular collar 200 is positioned above the series of slots 50c, the chamfered edges 58c of the wall 46c will guide the annular collar 200 into the slot 50c.

The present embodiment of the retainer 20c, as mentioned above, may also be used with the above-described adaptor 22 having the clip 34. A nurse uses the present retainer with the above-described adaptor 22 in the same manner as described above in connection with the above-described retainer 20.

If the catheter hub 30 (see FIG. 1) is a standard female lure-lock fitting, the lure-lock fitting 220 (FIG. 14) of the adaptor body 22d is rotated with the distal end 26d inserted into the catheter hub 30 to interlock the corresponding fittings 222, 30 in the known manner. The catheter adaptor 22d is then used with the anchoring system in a like manner to that described above.

The above embodiments illustrate the adaptor with the radially extending member being affixed to an end of a tube set or other fluid line. The radially extending member can also be arranged on the adaptor or fitting that is affixed to the proximal end of the catheter body. FIGS. 15a through 15c illustrate this arrangement.

FIGS. 15a through 15c illustrate a catheterization system configured in accordance with another embodiment of the present invention. The catheterization system includes a catheter and an anchoring system that includes a retainer and an anchoring pad. Although the anchoring pad has been omitted from FIGS. 15a through 15c to simplify the drawings, the anchor pad desirably is constructed in accordance with the above description and is shaped in the form shown in FIG. 16. Again, for consistency, like numbers with an "e" suffix have been used to indicate like parts of the anchoring system of FIGS. 11 and of 15a-15c. The above description of like components thus should be understood as applying equally to the present embodiment, unless stated otherwise.

The catheter desirably includes an elongated tubular body with a tubular adaptor or fitting attached to the body. At least one lumen of the adaptor communicates with a corresponding lumen of the catheter. In the illustrated embodiment, the adaptor 22e is permanently attached to a proximal end of the fitting and is configured to cooperate with a corresponding adaptor formed on a distal end of a fluid line. The adaptor 22e, however, can be releasably attached to the catheter body.

In the illustrated embodiment, the tubular adaptor 22e is configured as a female-component of the coupling between the catheter body and the fluid line. The adaptor 22e of course can be configured as the male component of the coupling. In either case, both the male and female adaptors of the coupling have corresponding generally frusto-conical shapes which mate together in a generally fluid tight engagement. The coupling adaptors also include interengaging elements that lock together the adaptors. The tubular adaptor 22e of the illustrated embodiment includes a threaded coupler 306 formed by an external thread that runs about a proximal end 300 of a tubular body of the adaptor 22e. The external thread of the threaded coupler is configured to corresponding to an internal thread of a spin nut disposed on the end of the corresponding adaptor (such as the type illustrated in FIG. 14).

In the illustrated embodiment, the tubular body of the adaptor 22e includes a frusto-conical shaped section 304 on the distal side 302 of the threaded coupler 306. The corresponding form of the adaptor 22e generally corresponds to a conventional catheter hub, such as the type illustrated in FIG. 1.

Unlike a conventional catheter hub, however, the adaptor 22e includes a radially extending member that projects from the tubular body. In the illustrated embodiment, the radially extending member comprises an annular collar 200e that circumscribes a portion of the frusto-conical shaped section 304 of the tubular body. The collar 200e is generally positioned about midway between the proximal and distal ends 300, 302 of the tubular body; however, it need not be as illustrated in embodiment of FIG. 16.

As understood from FIGS. 15a through 15c, the retainer 20e defines a central channel 44e that has a generally conical shape corresponding to the shape of the adaptor tubular body. The channel 44e is interposed between a pair of opposing converging longitudinal walls 46e.

The walls 46e are spaced apart such that there is a variable lateral distance therebetween. The walls 46e have a proximal end 300 and a distal end 302, with the proximal end width being desirably wider than the distal end width.

The central channel 44e extends through the retainer 20e along the longitudinal axis and between the converging walls 46e. The channel 44e is similarly of variable lateral dimension as taken at points along the longitudinal axis direction.

The central channel 44e has a truncated upper section which gives the channel a generally U-shape having an upper opening 47e. The bottom and side surfaces of the channel 44e are arcuate and substantially match the shape of the catheter adaptor 22e, which can be received therein. The variable diameter of the channel 44e is sized to receive the longitudinal length of the catheter adaptor 22e. Each section of the channel 44e has arcuate shape of a radius of curvature that generally matches a corresponding section of the catheter adaptor 22e. In the illustrated embodiment, the radii of curvature vary along the longitudinal length of the channel 44e; however, the channel 44e can have generally uniform radii of curvature, as illustrated by the above embodiments.

In cross section, as best understood from FIG. 15c, the channel 44e extends through an arc of greater than 180° about the longitudinal axis such that the lateral length of the upper opening 47e is less than the diameter of the channel 44e at a given point in the longitudinal direction. In the illustrated embodiment, the channel 44e desirably extends through an arc of about 200° about the channel axis.

The retainer also includes at least one slot 50e that lies generally perpendicular to the longitudinal axis and extends across the channel 44e to section the channel 44e into a proximal channel portion and a distal channel portion. In the illustrated embodiment, the proximal and distal channel portions have generally equal longitudinal lengths; however, they need not have the same length. The length of the channel portions though desirably provides stability to the catheter adaptor 22e when inserted into the retainer 20e to prevent the catheter adaptor 22e from yawing (i.e. pivoting relative to the retainer within a plane parallel to the anchor pad). Each channel section of the retainer 20e is also sized to receive a corresponding section of the catheter adaptor 22e. Each slot 50e is sized to receive the collar 200e of the catheter adaptor 22e.

The slot 50e has a thickness that substantially matches the thickness of the adaptor collar 200e. The thickness of slot 50e, however, is less than the combined longitudinal lengths of the proximal and distal channel portions. This dimensional relationship provides further stability to the retained catheter adaptor 22e when inserted into the retainer 20e.

In the illustrated embodiment, the retainer 20e includes at least two lateral slots 50e arranged in series (i.e., next to each other) between the proximal and distal channel portions. The series of slots desirably includes between two (2) and twenty (20) slots. More preferably, the series comprises less than seven (7) slots. The illustrated embodiment shows two (2) slots.

As described above, each slot 50e is sized to receive a portion of the adaptor annular collar 200c to prevent longitudinal displacement of the catheter, as discussed in detail above. Each slot 50e desirably has a rectangular shape and extends from an exterior surfaces 52e through the walls 46e, and across the central channel 46e. The width of each slot 50e (measured longitudinally) is desirably slightly greater than the width of the fitting 304, measured in the longitudinal direction to receive the fitting 304, as discussed above.

The retainer 20e also desirably includes a relief 308 formed on the bottom of the channel 44e. The relief 308 is sized to receive a portion of the collar 200e when placed within one of the slots 50e.

Finger platforms 310 extend from the side walls 46e of the retainer 20e. The finger platforms 310 are sized and configured to enable allow a health care provider to press the retainer 20e against the skin of the patient while pulling up on the catheter adaptor 22e or on the adaptor to which it is connected, when disengaging the catheter adaptor 22e from the retainer 20e.

So configured, in addition to the interengagement between the slots 50e and annular collar 200e, longitudinal movement of the catheter in the proximal-to-distal direction is further inhibited by cooperation between the conical-shaped channel 44e and frusto-conical shaped fitting 304. That is, when an applied force directs the fitting 304 in the distal direction, the fitting 304 advances until contact with a section of the walls 46e (which are of uniformly narrower diameter as measured toward the proximal end of the walls 46e). When contact is made, the fitting 304, and catheter which is attached thereto, is restricted from further distal movement.

FIG. 16 illustrates another embodiment of the catheterization system similar to that described above in connection with FIGS. 15a-15c. Accordingly, like reference numerals with a "f" suffix have been used to indicate similar components between these embodiments. The above description of like components thus applies equally to the present embodiment, unless stated otherwise.

In the illustrated embodiment, the conical shaped section of the catheter hub 304 has an irregular step in diameter between the side proximal 300f of the collar 200f and the side distal 302f of the collar 200f. That is a minimum diameter of the conical section on the side proximal 300f the collar 200f is larger than a maximum diameter of the conical section on the side distal 302f of the collar 200f.

The retainer 20f has a shape corresponding to that of the conical section of the catheter adaptor 22f. The proximal 300f channel portion has a radius of curvature generally matching that of the proximal 300f side of the adaptor conical section. And the distal 302f channel portion has a radius of curvature generally matching that of the distal 302f side of the adaptor conical section. As such, a minimum diameter of the proximal 300f channel section is larger than a maximum diameter of the distal 302f channel section.

The retainer 20f is mounted atop an anchor pad 16f with its upper opening 47f being exposed and facing away from the anchor pad 16f. The construction of the anchor pad 16f and the retainer 20f, as well as the attachment of the retainer 20f to the anchor pad 16f, are in accordance with the above description. The anchor pad 16f also supports a tube clip 24f, as illustrated in FIG. 16.

As similar to the above embodiment, the present catheterization system is used by first connecting the catheter to a fluid line (be it supply or drainage). The catheter is inserted into a body lumen, such as a vein, in accordance with the above description. The nurse then inserts a distal end of one of the coupling adaptor 22c into a catheter adaptor to connect together the adaptors. The nurse may then interconnect the adapters by means of the above-described ratchet clip, or the lure-lock fitting formed between the threaded coupler on the proximal end of the catheter adaptor and the spin nut on the end of the adaptor attached to the fluid tube.

The nurse removes the paper backing which initially covers an adhesive bottom surface of the anchor pad 16f, as described above, and attaches the anchor pad 16f to the patient's skin proximate to the indwelling catheter. The nurse specifically positions a notch of the pad 16f around the catheter body or cannula. The nurse generally aligns the proximal edge of the anchor pad 16f with the insertion site.

The nurse positions the adaptor 22f above the series of retainer slots 50f, and snaps the adaptor 22f into the retainer 20f. In doing so, the adaptor 20f is pressed between the longitudinal walls 46f of the retainer 20f with the annular collar 200f extending into one of the slots 50f of the retainer 20f. As the nurse presses the adaptor 22f into the retainer 20f, chamfered edges 312 around the slots 50f (see FIG. 15a) of the longitudinal walls 46f guide the annular collar 200f into the slots 50f. With the annular collar 200f positioned in one of the slots 50f, the adaptor 22f is prevented from sliding in a longitudinal direction.

Like the above-described embodiments of the retainer 20f, the ergonomic design of the retainer 20f provides for various positions of the adaptor 22f in the retainer 20f so that the retainer 20f is not technique- or position-sensitive. That is, a nurse can simply press the adaptor 22f into the retainer 20f, irrespective of the position of the annular collar 200f relative to a particular slot 50f of the retainer 20f. So long as the annular collar 200f is positioned above the series of slots 50f, the chamfered edges 312 of the wall will guide the annular collar 200f into the slot 50f.

Figure 17:
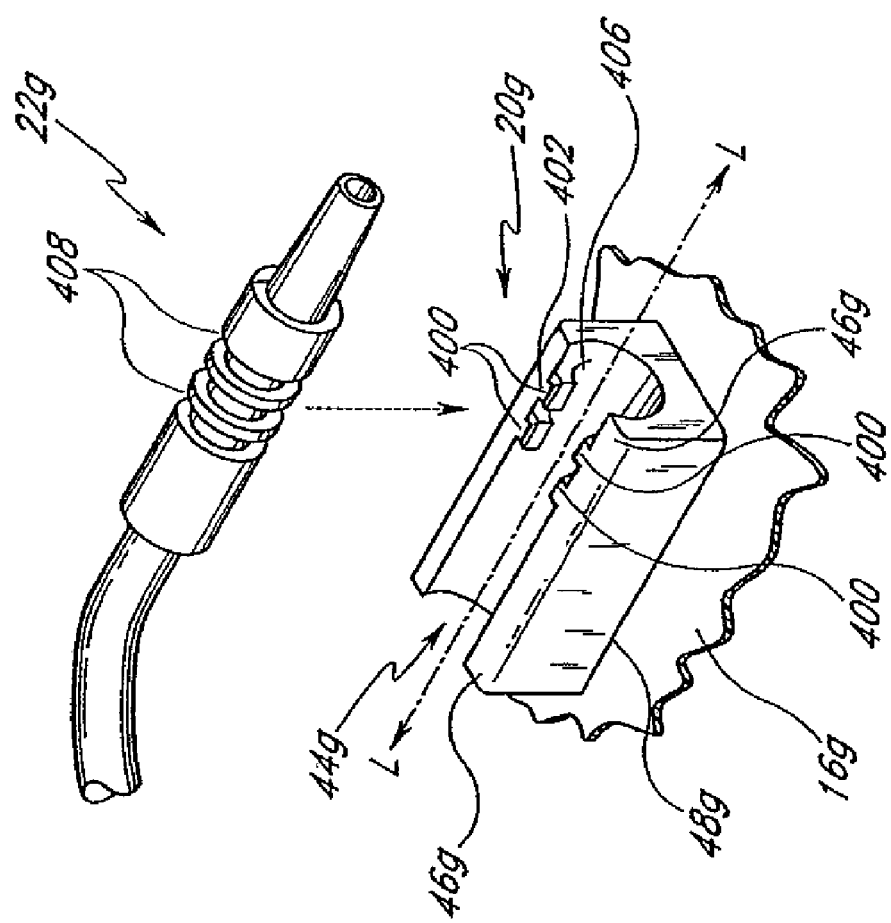
FIG. 17 is a perspective view of a catheterization system configured in accordance with another embodiment of the present invention, and illustrates the a catheter adaptor having a plurality of radial recesses and a retainer having a plurality of projections that cooperate with the recesses when the retainer receives the catheter adaptor.
Figure 18:
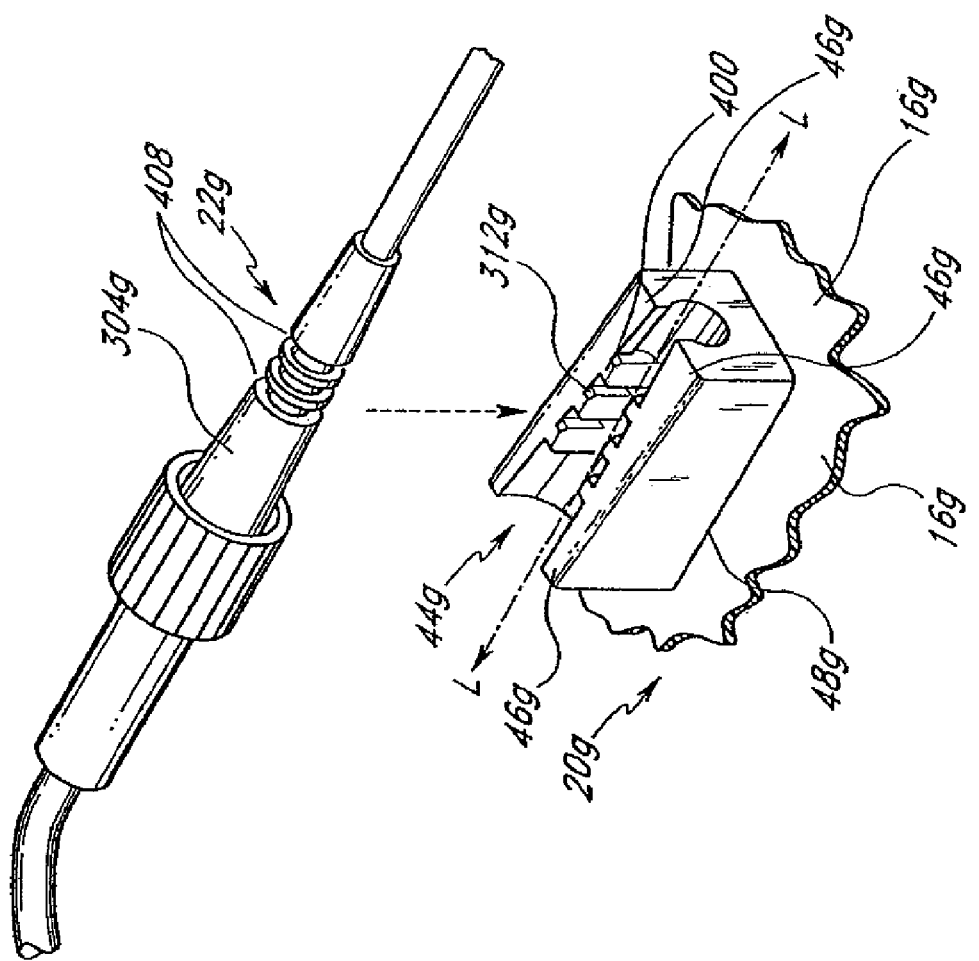
FIG. 18 is a perspective view of the catheterization system configured in accordance with an additional embodiment of the present invention, and illustrates the catheter adaptor having a plurality of radial recesses and a retainer having a plurality of projections that extend into a channel having a tapered diameter.

FIGS. 17 and 18 illustrate a catheterization system configured in accordance with another embodiment of the present invention. Like the other embodiments of the catheterization system, this embodiment includes a catheter and an anchoring system that includes a retainer and an anchoring pad. Again, for consistency, like numbers with an "g" suffix have been used to indicate like parts of the anchoring system of FIGS. 11 and of 16. The above description of like components thus should be understood as applying equally to this embodiment, unless stated otherwise.

The present embodiment, like the previous embodiments, utilizes the concept of providing an adaptor and retainer which cooperate with each other to secure the catheter to the body of a patient and inhibit movement of the catheter in the longitudinal, transverse and lateral directions. Also, like the previous embodiments, the anchoring system can include the concept of not being position or technique sensitive. That is, the medical attendant can simply locate the catheter adaptor generally above the retainer and press the adaptor into the retainer. Engagement thus requires only coarse alignment of the adaptor with the retainer.

FIG. 17 shows the retainer 20g comprising a longitudinal channel 44g formed between a pair of substantially parallel walls 46g and configured to receive the tubular body of the adaptor 22g in a snap fit manner. The construction of the channel thus is similar to that described above and about a longitudinal axis L.

The retainer 20g additionally comprises at least one projection or protuberance 400 that extends from one of the walls 46g toward the longitudinal axis in the lateral direction. The projection 400 is sized and configured to cooperate with a recess on the catheter adaptor 22g, as explained below. The projection 400, however, can extend into the channel 44g toward the longitudinal axis in the transverse direction.

In the illustrated embodiment, the retainer 20g includes a plurality of projections 400. In one mode, two projections are positioned across from each other on opposite walls 46g. The set of projections 400 thus oppose each other. The retainer 20g also desirably includes a plurality of projection sets 400 which are spaced along a length of the channel 44g. The multiple projection sets 400 thus provide multiple positions in which the adaptor 22g can occupy within the retainer 20g, so as to require only coarse alignment between the retainer 20g and the adaptor 22g before engagement. Both laterally and transversely extending projections 400 can be used with the retainer.

The projections 400 desirably are positioned between a first portion of the channel 44g and a second portion of the channel 44g. In the illustrated embodiment, one channel portion is formed at a proximal end of the channel 44g and the other end is formed at a distal end of the channel 44g. Each of the channel portions desirably are sufficiently long and support a sufficient length of the adaptor 22g so as to prevent the adaptor 22g from rocking.

Each projection 400 desirably has sufficient thickness or bulk so as to resist nominal applied forces, i.e. not break when the medical attendant presses on it. Also, the portion of the projection 400 that projects into the channel 44g is of sufficient lateral or transverse dimension to inhibit movement of the catheter adaptor 22g in the longitudinal direction, without inhibiting placement of the catheter adaptor 22g into or out of the channel 44g. That is, the projections 400 extend into the channel by a sufficient amount to engage with corresponding structure on the catheter adaptor 22g, as described below.

In the illustrated embodiment, each projection 400 has generally a rectangular shape in a plane generally parallel to the retainer base 48g. Thus, the projections 400 generally form a series of square teeth along a section of each wall 46g at an upper rim of the channel 44g. The projection 400, however, can be configured in a wide variety of other shapes, including, but not limited to, semi-circular, square, curvilinear, triangular or the like. Thus, the projection 400 may be linear, as illustrated, or curved or curvilinear to suit a particular application, so as to inhibit migration of the catheter adaptor 22g in the longitudinal direction.

Below the upper rim of the channel 44g, each projection tapers back toward the corresponding side wall 46g. In the illustrated embodiment, this taper 406 generally follows an arcuate path that desirably corresponds to a surface to the adaptor 22g, as described below. The projections 400, however, can extend about the entire arc of the channel 44g (i.e., down one side wall, across the bottom of the channel and up the other side wall) or the projections 400 can extend downward to the channel bottom (FIG. 18).

As noted above, the projections 400 are advantageously sized and configured to cooperate with a corresponding recess(es) on the catheter adaptor 22g. Without limitation, the catheter adaptor 22g can be a fitting on the end of either the fluid tube, as shown in FIG. 17, or the catheter as shown in FIG. 18 (e.g., a catheter hub).

In one mode, the projections 400 fit into the recess(es) and engage the sides of the recess(es) so as to inhibit longitudinal movement of the adaptor 22g relative to the retainer 20g. In the illustrated embodiment, the adaptor 22g includes a plurality of annular grooves or depressions 408 (e.g., three grooves); however, any number of annular grooves 408 can be used with the adaptor 22g. In order to accommodate the adaptor 22g in multiple positions within the retainer 20g, however, the number of projection sets 400 should be less than the number of grooves 408.

Each annular groove 408 is interposed between the proximal and distal ends 28g, 26g of the adaptor 22g and extends radially inward while circumscribing the adaptor 22g. Each annular groove 408 also has a thickness measured in the longitudinal direction which is slightly less than the longitudinal length of the projection 400 so that at least a portion of the annular depression 408 fits around the projection 408 of the retainer wall 46g, as described above.

Each annular groove 408 thus defines an arcuate surface on the exterior of the adaptor 22g. In the illustrated embodiment, the radius of this arcuate surface desirably is not greater than the radius of curvature followed by the corresponding projection(s) 400 as it tapers toward the respective wall 46g, as noted above.

FIG. 18 is generally similar to FIG. 17 except that the retainer 20g is configured to receive a frusto-conical shaped section 304g of the adaptor 22g, rather than an adaptor 22g having a uniform diameter, as shown in FIG. 17. To form the snap fit engagement between the retainer 20g and tapered adaptor 22g, the channel 44g extends through the retainer 20g along the longitudinal axis and between converging walls 46g, thus forming a tapered or stepped region. The illustrated embodiment also shows four projections 400 formed on the retainer 20g, however, it is understood that any suitable number of projections (2-20) can be used with the retainer 20g.

The present embodiment of the catheterization system is used by first catheter is inserted into a body lumen, such as a vein, in accordance with the above description. The medical attendant then connects the catheter adaptors together so as to attach the catheter to the fluid line. The medical attendant may then interconnect the adapters by means of the above-described ratchet clip, or the lure-lock fitting formed between the threaded coupler on the proximal end of the catheter adaptor and the spin nut on the end of the adaptor attached to the fluid tube.

The medical attendant positions the adaptor 22g above the series of retainer projections 400, and snaps the adaptor 22g into the retainer 20g. In doing so, the adaptor 22g is pressed between the longitudinal walls 46g of the retainer 20g with at least a portion of the annular depression 408 receiving a corresponding projection 400. With at least a portion of the annular depression 408 positioned around one of the projections 400, the adaptor 22g is inhibited from moving in a longitudinal direction. The medical attendant then removes the paper backing which initially covers an adhesive bottom surface of the anchor pad 16g and attaches the anchor pad 16g to the patient's skin proximate to the indwelling catheter, as described above.

As previously explained, the ergonomic design of the retainer 20g provides for various positions of the adaptor 22g in the retainer 20g so that the retainer 20g is not technique or position sensitive. That is, a medical attendant can simply press the adaptor 22g into the retainer 20g, irrespective of the position of the annular depression 408 relative to a particular projection 400 of the retainer 20g. Further, so long as the annular depression 408 is positioned above the series of projections 400, the chamfered edges 312g of the wall 46g will guide the annular depression around at least a portion of the projection 400.

Although this invention has been described in terms of certain preferred embodiments, other embodiments apparent to those of ordinary skill in the art are also within the scope of this invention. It is also understood that various aspects of one embodiments can between with another embodiment. Accordingly, the scope of the invention is intended to be defined only by the claims which follow.

What is claimed is:

1. A securement device for attaching a medical article to a patient, the medical article having a generally elongated body and a side member that projects away from the body, the securement device comprising:
a retainer having a first channel portion and a second channel portion, the channel portions being disposed about a longitudinal axis of the retainer and having a length measured in a direction parallel to the longitudinal axis of the retainer, the retainer directly contacting the medical article along at least a substantial portion of the longitudinal lengths of the first and second channel portions, each channel portion curving about the longitudinal axis of the retainer by greater than 180°, the first channel portion being spaced from the second channel portion, at least part of the first channel portion being wider, as measured perpendicularly to the longitudinal axis of the retainer, than another part of the first channel portion, the combined longitudinal lengths of the first and second channel portions being larger than a distance separating the first and second channel portions along the longitudinal axis of the retainer, said distance substantially equaling a dimension of the side member of the medical article as measured parallel to the longitudinal axis of the retainer;
a base, the retainer being coupled to the base so as to move in a longitudinal direction relative to the base; and
an interlocking mechanism, at least a portion of the interlocking mechanism being movable in a direction perpendicular to the longitudinal direction so as to limit the retainer from moving relative to the base.

2. A securement device according to claim 1, wherein at least one of the channel portions is exposed though a longitudinally extending opening.

3. A securement device according to claim 1, wherein each channel portion defines a longitudinally extending opening.

4. A securement device according to claim 3, wherein each opening has a width less than a width of the corresponding channel portion.

5. A securement device according to claim 1 further comprising a flexible anchor having an adhesive bottom surface and a top surface above which the retainer is disposed.

6. A securement device according to claim 5, wherein each channel portion includes a longitudinal opening and the retainer is disposed in a position above the top surface so as to expose the openings to the channel portions.

7. A securement device according to claim 5, wherein the longitudinal axis of the retainer is disposed at an acute angle relative to the anchor.

8. A securement device according to claim 1, wherein at least one of the first and second channel portions has a truncated generally circular cross-sectional shape.

9. A securement device according to claim 1, wherein the cross-section of at least one of the first and second channel portions tapers in size along its length.

10. A securement device according to claim 1, wherein at least one of the first and second channel portions has a generally frusto-conical shape.

11. A securement device according to claim 1, wherein the distance separating the first and second channel portions forms a continuous gap which extends around the longitudinal axis of the retainer for at least 180 degrees.

12. A securement device according to claim 1, wherein the retainer further comprises a pair of opposing surfaces from which the first and second channel portions extend in opposite directions along the longitudinal axis.

13. A securement device according to claim 12, wherein the opposing surfaces are generally perpendicular to the longitudinal axis.

14. A securement device according to claim 1, wherein the direct contact between the medical article and at least one of the first and second channel portions is discontinuous along the longitudinal length of the at least one of the first and second channel portions.

15. A securement device for attaching a medical article to a patient, the medical article having a generally elongated body and a side member that projects away from the body, the securement device comprising:
an anchor pad;
a base affixed to the anchor pad; and
a retainer movably coupled to the base so as to move in a longitudinal direction relative to the base, the retainer comprising at least first and second channel portions arranged side-by-side along a longitudinal axis of the retainer with at least one gap occurring between the channel portions, the gap having a dimension in a direction parallel to the longitudinal axis of the retainer that generally matches a dimension of the side member of the medical article as measured parallel to the longitudinal axis of the retainer; and
an interlocking mechanism, at least a portion of the interlocking mechanism being movable in a direction perpendicular to the longitudinal direction so as to limit the retainer from moving relative to the base.

16. A securement device according to claim 15, wherein at least one of the channel portions is exposed though a longitudinally extending opening.

17. A securement device according to claim 15, wherein each channel portion defines a longitudinally extending opening.

18. A securement device according to claim 17, wherein each opening has a width less than a width of the corresponding channel portion, where said widths are measured perpendicularly to the longitudinal axis of the retainer.

19. A securement device according to claim 18, wherein the retainer is disposed above the base and in a position that exposes the openings to the channel portions.

20. A securement device according to claim 15, wherein the anchor pad comprises an adhesive bottom surface and a top surface above which the base is disposed.

21. A securement device according to claim 20, wherein the longitudinal axis of the retainer is disposed at an acute angle relative to the bottom surface of the anchor pad.

22. A securement device according to claim 15, wherein the cross-section of at least one of the first and second channel portions tapers in size along its length.

23. A securement device according to claim 15, wherein at least one of the first and second channel portions has a generally frusto-conical shape.

24. A securement device according to claim 15, wherein said gap is defined by a pair of opposing surfaces.

25. A securement device according to claim 24, wherein the opposing surfaces lie generally perpendicularly to the longitudinal axis of the retainer.

26. A securement device according to claim 15, wherein the distance separating the first and second channel portions forms a continuous gap which extends around the longitudinal axis of the retainer for at least 180 degrees.

27. A securement device according to claim 15, wherein at least one of the first and second channel portions extends about the longitudinal axis of the retainer by greater than about 180°.

28. A securement device according to claim 15, wherein the first channel portion of the retainer has a truncated circular cross-sectional shape and surrounds at least a portion of the medical article through an arc of greater than 180 degrees about the longitudinal axis of the first channel portion when the medical article is received by the first channel portion.

29. A securement device according to claim 15, wherein at least part of the first channel portion is wider, as measured perpendicularly to the longitudinal axis of the retainer, than the second channel portion.

30. A securement device for attaching a medical article to a patient, the medical article having a generally elongated body and a side member that projects away from the body, the securement device comprising:
- a retainer including first and second channel portions that each curve about a longitudinal axis of the retainer by more than 180°, the retainer directly contacting the medical article along at least a substantial portion of the longitudinal lengths of the first and second channel portions, each channel portion having an opening that extends along the longitudinal axis of the retainer, the first and second channel portions being disposed apart with at least one gap therebetween, a distance across the gap as measured in a direction parallel to the longitudinal axis of the retainer being substantially the same as a dimension of the side member of the medical article, which is measured along the longitudinal axis of the retainer, and being less than the combined lengths of the first and second channel portions as measured parallel to the longitudinal axis of the retainer;
- a base, the retainer being coupled to the base so as to move in a longitudinal direction relative to the base;
- an interlocking mechanism, at least a portion of the interlocking mechanism being movable in a direction perpendicular to the longitudinal direction so as to limit the retainer from moving relative to the base; and
- a flexible anchor having a bottom surface with an adhesive for attaching the anchor to the patient, the base being coupled to the anchor.

31. A securement device according to claim 30, wherein at least one of the first and second channel portions has a truncated circular cross-sectional shape.

32. A securement device according to claim 30, wherein the cross-section of at least one of the first and second channel portions tapers in size along its length.

33. A securement device according to claim 30, wherein at least one of the first and second channel portions has a generally frusto-conical shape.

34. A securement device according to claim 30, wherein said gap is defined by a pair of opposing surfaces.

35. A securement device according to claim 34, wherein the opposing surfaces generally lie perpendicular to the longitudinal axis of the retainer.

36. A securement device according to claim 30, wherein the direct contact between the medical article and at least one of the first and second channel portions is discontinuous along the longitudinal length of the at least one of the first and second channel portions.

* * * * *